US009254133B2

(12) United States Patent  
Zhang et al.

(10) Patent No.: US 9,254,133 B2
(45) Date of Patent: Feb. 9, 2016

(54) STERILIZED LIQUID COMPOSITIONS OF CYANOACRYLATE MONOMER MIXTURES

(71) Applicant: Adhezion Biomedical, LLC, Wyomissing, PA (US)

(72) Inventors: Sheng Zhang, Hickory, NC (US); Rafael Ruiz, Sr., Hudson, NC (US)

(73) Assignee: Adhezion Biomedical, LLC, Wyomissing, PA (US)

( * ) Notice: Subject to any disclaimer, the term of this patent is extended or adjusted under 35 U.S.C. 154(b) by 19 days.

(21) Appl. No.: 14/182,500

(22) Filed: Feb. 18, 2014

(65) Prior Publication Data

US 2014/0163610 A1 Jun. 12, 2014

Related U.S. Application Data

(63) Continuation-in-part of application No. 13/953,011, filed on Jul. 29, 2013, now Pat. No. 8,652,510, which is a continuation-in-part of application No. 12/378,277, filed on Feb. 12, 2009, now Pat. No. 8,609,128.

(60) Provisional application No. 61/197,954, filed on Oct. 31, 2008.

(51) Int. Cl.
| | |
|---|---|
| A61F 13/00 | (2006.01) |
| A61B 17/10 | (2006.01) |
| A61L 15/24 | (2006.01) |
| A61L 15/44 | (2006.01) |
| A61L 15/58 | (2006.01) |
| A61L 26/00 | (2006.01) |
| C09D 133/20 | (2006.01) |
| A61M 25/04 | (2006.01) |

(52) U.S. Cl.
CPC ............ *A61B 17/10* (2013.01); *A61L 15/24* (2013.01); *A61L 15/44* (2013.01); *A61L 15/58* (2013.01); *A61L 26/0014* (2013.01); *A61L 26/0066* (2013.01); *C09D 133/20* (2013.01); *A61L 2300/404* (2013.01); *A61M 25/04* (2013.01); *C08L 2203/02* (2013.01)

(58) Field of Classification Search
None
See application file for complete search history.

(56) References Cited

U.S. PATENT DOCUMENTS

| 211,104 A | 1/1879 | Mulford |
|---|---|---|
| 334,046 A | 1/1886 | Pinkham |
| 1,221,227 A | 4/1917 | Shulz |
| 1,229,195 A | 6/1917 | Hamilton |
| 1,234,844 A | 7/1917 | Williams |
| 1,822,566 A | 9/1931 | Davies |
| 2,333,070 A | 10/1943 | Hoey et al. |
| 2,721,858 A | 10/1955 | Joyner et al. |
| 2,794,788 A | 6/1957 | Coover, Jr. et al. |
| 2,912,454 A | 11/1959 | McKeever |
| 3,152,352 A | 10/1964 | Kosik, Jr. |
| 3,254,111 A | 5/1966 | Hawkins et al. |
| 3,260,637 A | 7/1966 | von Bramer |
| 3,282,773 A | 11/1966 | Wicker, Jr. et al. |
| 3,324,855 A | 6/1967 | Heimlich |
| 3,393,962 A | 7/1968 | Andrews |
| 3,451,538 A | 6/1969 | Trementozzi |
| 3,523,628 A | 8/1970 | Colvin et al. |
| 3,524,537 A | 8/1970 | Winter |
| 3,527,224 A | 9/1970 | Rabinowitz |
| 3,527,841 A | 9/1970 | Wicker, Jr. et al. |
| 3,540,577 A | 11/1970 | Trementozzi et al. |
| 3,564,078 A | 2/1971 | Wicker, Jr. et al. |
| 3,579,628 A | 5/1971 | Gander et al. |
| 3,607,542 A | 9/1971 | Leonard et al. |
| 3,614,245 A | 10/1971 | Schwartzman |
| 3,667,472 A | 6/1972 | Halpern |
| 3,692,752 A | 9/1972 | Setsuda et al. |
| 3,742,018 A | 6/1973 | O'Sullivan |
| 3,779,706 A | 12/1973 | Nablo |
| 3,797,706 A | 3/1974 | Mule |
| 3,836,377 A | 9/1974 | Delahunty |
| 3,863,014 A | 1/1975 | Mottus |
| 3,903,055 A | 9/1975 | Buck |
| 3,924,623 A | 12/1975 | Avery |
| 3,941,488 A | 3/1976 | Maxwell |
| 3,975,422 A | 8/1976 | Buck |

(Continued)

FOREIGN PATENT DOCUMENTS

| DE | 2 261 261 | 7/1973 |
|---|---|---|
| DE | 40 09 621 | 10/1991 |

(Continued)

OTHER PUBLICATIONS

"Aclare/Barex® Laminates: Flexible Solutions for Pharma Packaging" Drug Delivery Technology vol. 3, No. 3, May 2003, Posted on Mar. 28, 2008, http://www.drugdeliverytech.com/ME2/dirmod.asp?sid=&nm=&type=Publishing&mod=Publications%3A%3AArticle&mid=8F3A7027421841978F18BE895F87F791&tier=4&id=6EC6964EB29D46D8A297E499E57A4164.

Borrel et al. "The Effect of Crown Ethers, Tetraalkylammonioum Salts, and Polyoxyethylene Amphiphiles on Pirarubicin Incorporation in K562 Resistant Cells" Biochemical Pharmacology, vol. 50, No. 12., pp. 2069-2076, 1995.

Cameron, J.L. et al., "The Degradation of Cyanoacrylate Tissue Adhesive, pt. 1", Surgery, vol. 58, Iss. 2, Aug. 1965, pp. 424-430.

Canale, A.J., et al., "Methyl a-cyanoacrylate. I. Free-radical homopolymerization", Journal of Applied Polymer Science, vol. 4, No. 11, Sep./Oct. 1960, pp. 231-236 [Abstract Only].

(Continued)

*Primary Examiner* — David J Blanchard
*Assistant Examiner* — Daniel F Coughlin
(74) *Attorney, Agent, or Firm* — Stradley Ronon Stevens & Young, LLP

(57) ABSTRACT

Cyanoacrylate adhesive compositions comprise a mixture of two cyanoacrylate monomers, including 2-octyl cyanoacrylate and n-butyl cyanoacrylate. The monomers are stabilized and sterilized by irradiation, and do not substantially increase in viscosity after sterilization or after two years of shelf storage. These compositions have anti-microbial properties, and may be used to close wounds as well as secure catheters inserted into the body in place.

18 Claims, No Drawings

(56) References Cited

U.S. PATENT DOCUMENTS

| | | |
|---|---|---|
| 3,995,641 A | 12/1976 | Kronenthal et al. |
| 4,003,942 A | 1/1977 | Buck |
| 4,012,402 A | 3/1977 | Buck |
| 4,013,703 A | 3/1977 | Buck |
| 4,038,345 A | 7/1977 | O'Sullivan et al. |
| 4,041,063 A | 8/1977 | Buck |
| 4,042,442 A | 8/1977 | Dombroski et al. |
| 4,057,535 A | 11/1977 | Lipatova et al. |
| 4,102,945 A | 7/1978 | Gleave |
| 4,105,715 A | 8/1978 | Gleave |
| 4,109,037 A | 8/1978 | Nohara |
| 4,142,630 A | 3/1979 | Hayes et al. |
| 4,170,585 A | 10/1979 | Motegi et al. |
| 4,171,416 A | 10/1979 | Motegi et al. |
| 4,182,823 A | 1/1980 | Schoenberg |
| 4,265,948 A | 5/1981 | Hayes et al. |
| 4,310,509 A | 1/1982 | Berglund et al. |
| 4,323,557 A | 4/1982 | Rosso et al. |
| 4,328,170 A | 5/1982 | Okawara et al. |
| 4,340,043 A | 7/1982 | Seymour |
| 4,364,876 A | 12/1982 | Kimura et al. |
| 4,374,126 A | 2/1983 | Cardarelli et al. |
| 4,377,490 A | 3/1983 | Shiraishi et al. |
| 4,386,193 A | 5/1983 | Reich et al. |
| 4,413,753 A | 11/1983 | Stock |
| 4,439,196 A | 3/1984 | Higuchi |
| 4,444,933 A | 4/1984 | Columbus et al. |
| 4,447,224 A | 5/1984 | DeCant, Jr. et al. |
| 4,447,233 A | 5/1984 | Mayfield |
| 4,460,759 A | 7/1984 | Robins |
| 4,475,916 A | 10/1984 | Himmelstein |
| 4,480,940 A | 11/1984 | Woodruff |
| 4,486,194 A | 12/1984 | Ferrara |
| 4,487,603 A | 12/1984 | Harris |
| 4,533,422 A | 8/1985 | Litke |
| 4,542,012 A | 9/1985 | Dell |
| 4,551,366 A | 11/1985 | Maruhashi et al. |
| 4,554,686 A | 11/1985 | Baker |
| 4,643,181 A | 2/1987 | Brown |
| 4,646,765 A | 3/1987 | Cooper et al. |
| 4,649,909 A | 3/1987 | Thompson |
| 4,652,763 A | 3/1987 | Nablo |
| 4,685,591 A | 8/1987 | Schaefer et al. |
| 4,713,235 A | 12/1987 | Krall |
| 4,718,966 A | 1/1988 | Harris et al. |
| 4,772,148 A | 9/1988 | Buschemeyer |
| 4,786,534 A | 11/1988 | Aiken |
| 4,818,325 A | 4/1989 | Hiraiwa et al. |
| 4,925,678 A | 5/1990 | Ranney |
| 4,959,217 A | 9/1990 | Sanders et al. |
| 4,977,892 A | 12/1990 | Ewall |
| 4,978,527 A | 12/1990 | Brink et al. |
| 4,994,542 A | 2/1991 | Matsuda et al. |
| 5,009,654 A | 4/1991 | Minshall et al. |
| 5,039,753 A | 8/1991 | Woods et al. |
| 5,042,690 A | 8/1991 | O'Meara |
| 5,051,256 A | 9/1991 | Barnes |
| 5,069,907 A | 12/1991 | Mixon et al. |
| 5,083,685 A | 1/1992 | Amemiya et al. |
| 5,131,777 A | 7/1992 | Kimura et al. |
| 5,135,964 A | 8/1992 | Lee et al. |
| 5,167,616 A | 12/1992 | Haak et al. |
| 5,169,383 A | 12/1992 | Gyory et al. |
| 5,192,536 A | 3/1993 | Huprich |
| 5,225,182 A | 7/1993 | Sharma |
| 5,232,774 A | 8/1993 | Otsuka et al. |
| 5,236,703 A | 8/1993 | Usala |
| 5,240,525 A | 8/1993 | Percec et al. |
| 5,254,132 A | 10/1993 | Barley et al. |
| 5,283,034 A | 2/1994 | Okrongly et al. |
| 5,288,159 A | 2/1994 | Wirt |
| 5,302,629 A | 4/1994 | Berejka |
| 5,306,490 A | 4/1994 | Barley, Jr. |
| 5,312,864 A | 5/1994 | Wenz et al. |
| 5,328,687 A | 7/1994 | Leung et al. |
| 5,344,670 A | 9/1994 | Palmer et al. |
| 5,350,798 A | 9/1994 | Linden et al. |
| 5,358,349 A | 10/1994 | Burroughs et al. |
| 5,370,221 A | 12/1994 | Magnusson et al. |
| 5,403,591 A | 4/1995 | Tighe et al. |
| 5,411,345 A | 5/1995 | Ueji et al. |
| 5,453,457 A | 9/1995 | Meltzer et al. |
| 5,457,141 A | 10/1995 | Matsuda et al. |
| 5,470,597 A | 11/1995 | Mendenhall |
| 5,475,110 A | 12/1995 | Hudkins et al. |
| 5,480,935 A | 1/1996 | Greff et al. |
| 5,530,037 A | 6/1996 | McDonnell et al. |
| 5,547,662 A | 8/1996 | Khan et al. |
| 5,561,198 A | 10/1996 | Huver et al. |
| 5,665,817 A | 9/1997 | Greff et al. |
| 5,684,042 A | 11/1997 | Greff et al. |
| 5,730,994 A | 3/1998 | Askill et al. |
| 5,749,956 A | 5/1998 | Fisher et al. |
| 5,803,086 A | 9/1998 | Scholz et al. |
| 5,807,563 A | 9/1998 | Askill et al. |
| 5,874,044 A | 2/1999 | Kotzev |
| 5,902,594 A | 5/1999 | Greff et al. |
| 5,916,882 A | 6/1999 | Jeng |
| 5,928,611 A | 7/1999 | Leung |
| 5,944,754 A | 8/1999 | Vacanti |
| 5,957,877 A | 9/1999 | Askill et al. |
| 5,979,450 A | 11/1999 | Baker et al. |
| 5,981,621 A | 11/1999 | Clark et al. |
| 5,985,395 A | 11/1999 | Comstock et al. |
| 5,998,472 A | 12/1999 | Berger et al. |
| 6,086,906 A | 7/2000 | Greff et al. |
| 6,090,397 A | 7/2000 | Lee et al. |
| 6,099,807 A | 8/2000 | Leung |
| 6,136,326 A | 10/2000 | Kotzev |
| 6,143,352 A | 11/2000 | Clark et al. |
| 6,143,805 A | 11/2000 | Hickey et al. |
| 6,155,265 A | 12/2000 | Hammerslag |
| 6,217,603 B1 | 4/2001 | Clark et al. |
| 6,228,354 B1 | 5/2001 | Jeng |
| 6,245,933 B1 | 6/2001 | Malofsky et al. |
| 6,248,800 B1 | 6/2001 | Greff et al. |
| 6,294,629 B1 | 9/2001 | O'Dwyer et al. |
| 6,299,631 B1 | 10/2001 | Shalaby |
| 6,310,166 B1 | 10/2001 | Hickey et al. |
| 6,323,275 B2 | 11/2001 | Takahashi et al. |
| 6,342,213 B1 | 1/2002 | Barley et al. |
| 6,352,704 B1 | 3/2002 | Nicholson et al. |
| 6,488,665 B1 | 12/2002 | Severin et al. |
| 6,492,434 B1 | 12/2002 | Barley, Jr. et al. |
| 6,495,229 B1 | 12/2002 | Carte et al. |
| 6,547,917 B1 | 4/2003 | Misiak et al. |
| 6,579,469 B1 | 6/2003 | Nicholson et al. |
| 6,620,846 B1 | 9/2003 | Jonn et al. |
| 6,626,296 B1 | 9/2003 | Jimu et al. |
| 6,667,031 B2 | 12/2003 | Azevedo |
| 6,699,940 B2 | 3/2004 | Shalaby |
| 6,742,522 B1 | 6/2004 | Baker et al. |
| 6,743,858 B2 | 6/2004 | Hickey et al. |
| 6,746,667 B2 | 6/2004 | Badejo et al. |
| 6,767,552 B2 | 7/2004 | Narang |
| 6,779,657 B2 | 8/2004 | Mainwaring et al. |
| 6,797,107 B1 | 9/2004 | Kotzey |
| 6,802,416 B1 | 10/2004 | D'Alessio et al. |
| 6,849,082 B2 | 2/2005 | Azevedo |
| 6,881,421 B1 | 4/2005 | daSilveira et al. |
| 6,896,838 B2 | 5/2005 | D'Alessio |
| 6,942,875 B2 | 9/2005 | Hedgpeth |
| 6,960,040 B2 | 11/2005 | D'Alessio et al. |
| 6,974,585 B2 | 12/2005 | Askill |
| 6,977,278 B1 | 12/2005 | Misiak |
| 6,995,227 B2 | 2/2006 | Ryan et al. |
| 7,255,874 B1 | 8/2007 | Bobo et al. |
| 2002/0002223 A1 | 1/2002 | Cox et al. |
| 2002/0037272 A1 | 3/2002 | Askill et al. |
| 2003/0044380 A1 | 3/2003 | Zhu et al. |
| 2003/0077386 A1 | 4/2003 | Azevedo |
| 2003/0135016 A1 | 7/2003 | Tajima et al. |
| 2003/0149128 A1 | 8/2003 | Malofsky et al. |
| 2003/0158579 A1 | 8/2003 | Azevedo |

(56) References Cited

U.S. PATENT DOCUMENTS

| | | |
|---|---|---|
| 2003/0158580 A1 | 8/2003 | Azevedo |
| 2004/0115274 A1 | 6/2004 | Cox et al. |
| 2004/0120849 A1 | 6/2004 | Stewart et al. |
| 2004/0126355 A1 | 7/2004 | Childers |
| 2004/0127738 A1 | 7/2004 | Azevedo |
| 2004/0253039 A1 | 12/2004 | Stenton |
| 2005/0047846 A1 | 3/2005 | Narang et al. |
| 2005/0067312 A1 | 3/2005 | Gupta et al. |
| 2005/0142163 A1 | 6/2005 | Hunter et al. |
| 2005/0147582 A1 | 7/2005 | Zimmerman et al. |
| 2005/0182347 A1 | 8/2005 | Bishop et al. |
| 2005/0196431 A1 | 9/2005 | Narang et al. |
| 2005/0197421 A1 | 9/2005 | Loomis |
| 2005/0281866 A1 | 12/2005 | Jarrett et al. |
| 2005/0284487 A1 | 12/2005 | Gellerstedt et al. |
| 2006/0062687 A1 | 3/2006 | Morales |
| 2007/0041935 A1 | 2/2007 | Salamone et al. |
| 2007/0048356 A1 | 3/2007 | Schorr et al. |
| 2007/0078207 A1 | 4/2007 | Jonn et al. |
| 2007/0092481 A1 | 4/2007 | Misiak et al. |
| 2007/0092483 A1 | 4/2007 | Pollock |
| 2007/0147947 A1 | 6/2007 | Stenton et al. |
| 2007/0244490 A1 | 10/2007 | Moehle et al. |
| 2008/0021139 A1 | 1/2008 | Blacklock et al. |
| 2008/0078413 A1 | 4/2008 | Padget et al. |
| 2008/0102053 A1 | 5/2008 | Childers |
| 2008/0319063 A1 | 12/2008 | Zhang |
| 2009/0317353 A1 | 12/2009 | Zhang et al. |
| 2010/0035997 A1 | 2/2010 | Broadley et al. |
| 2010/0112036 A1 | 5/2010 | Zhang et al. |
| 2010/0269749 A1 | 10/2010 | Badejo et al. |
| 2012/0039838 A1* | 2/2012 | Zhang et al. ............... 424/78.06 |

FOREIGN PATENT DOCUMENTS

| | | |
|---|---|---|
| DE | 2010 3336 | 5/2001 |
| DE | 10 2007 019 044 | 10/2008 |
| EP | 0127466 | 12/1984 |
| EP | 0271675 | 6/1988 |
| FR | 2700698 | 7/1994 |
| GB | 1230560 | 5/1971 |
| GB | 2200124 | 7/1988 |
| JP | 59-066471 | 4/1984 |
| JP | 62-022877 | 1/1987 |
| JP | 03-207778 | 9/1991 |
| JP | 10-140091 | 5/1998 |
| WO | WO96/14292 | 5/1996 |
| WO | WO96/23532 | 8/1996 |
| WO | WO99/10020 | 3/1999 |
| WO | WO03/070257 | 8/2003 |
| WO | WO2004/045498 | 6/2004 |
| WO | WO2006/073922 | 7/2006 |
| WO | WO2009/003017 | 12/2008 |
| WO | WO2009/064291 | 5/2009 |

OTHER PUBLICATIONS

Collins et al., "Biological Substrates and Cure Rates of Cyanoacrylate Tissue Adhesives" Archives of Surgery vol. 93, Sep. 1966, 428-432.

Darwish et al., "The evaluation of crown ether based niosomes as cation containing and cation sensitive drug delivery systems" International Journal of Pharmaceutics 159 (1997) 207-213.

Dumont et al., "New Oligosaccharidic Crown Ethers as Potential Drug-Targetting Vectors: Synthesis & Biological Evaluation." Bioorganic & Medicinal Chemistry Letters, vol. 4, No. 9, pp. 1123-1126, 1994.

Fussnegger, B. "Poloxamers (1) Lutrol® F 68 (Poloxamer 188)." BASF ExAct, Nov. 1999, 5-6.

Garnier-Suillerot et al., "Analysis of Drug Transport Kinetics in Multidrug-resistant Cells: Implications for Drug Action" Current Medicinal Chemistry, 2001, 8, 51-64.

Hansen, "Fast Cure—High moisture vapor transmission rate adhesives improve wound care." Adhesives Age Mar. 2003, 22, 24-25.

International Search Report and Written Opinion dated Dec. 8, 2010 for international application No. PCT/US2009/062761.

Lehman et al., "Toxicity of Alkyl 2-Cyanoacrylates", Archives of Surgery, vol. 93, Issue 3, Sep. 1966, pp. 441-446.

Leonard, F, "Hemostatic Applications of Alpha Cyanoacrylates: Bonding Mechanism and Physiological Degradation of Bonds", Adhesion in Biological Systems, ed. R.S. Manly, 1970, pp. 185-199.

Leonard, F. et al., "Interfacial Polymerization of n-Alkyl a-Cyanoacrylate Homologs", Journal of Applied Polymer Science, vol. 10 1966, pp. 1617-1623.

Leonard, F. et al., "Synthesis and Degradation of Poly (alkyl a-Cyanoacrylates)", Journal of Applied Polymer Science, vol. 10, Iss 8, Aug. 1966, p. 1214.

Leonard, F. et al., "Synthesis and Degradation of Poly(alkyl a-Cyanoacrylates)", Journal of Applied Polymer Science, vol. 10, Iss. 2, Feb. 1966, pp. 259-272.

Material Safety Data Sheet (MSDS) of 2-octyl cyanoacrylate; Jun. 2, 2004.

Material Safety Data Sheet (MSDS) of isobuthyl-2-cyanoacrylate; Sep. 25, 1998.

Material Safety Data Sheet (MSDS) of n-butyl cyanoacrylate; Oct. 19, 2009 and Jun. 2, 2004.

Quinn, J.V., "Clinical Approaches to the Use of Cyanoacrylate Tissue Adhesives", Tissue Adhesives in Clinical Medicine, Second Edition, 2005, BC Decker, Inc., pp. 27-76.

Tseng, Y.C. et al., "Modification of synthesis and investigation of properties for 2-cyanoacrylates", Biomaterials, vol. 11, Jan. 1990, pp. 73-79.

Uchegbu et al., "Non-ionic surfactant based vesicles (niosomes) in drug delivery" International Journal of Pharmaceutics 172 (1998) 33-70.

Vezin, W.R. et al., "Diffusion of Small Molecules in Poly-n-Alkyl Cyanoacrylates", British Pharmaceutical Conference 1978—Communications presented at the 115th meeting, Coventry, Sep. 11-15, 1978, Journal of Pharmacy and Pharmacology, vol. 30, Issue: Suppl, Dec. 1978, p. 2P.

Vezin, W.R. et al., "In vitro heterogeneous degradation of poly(n-alkyl a-cyanoacrylates)", Journal of Biomedical Materials Research, vol. 14, 1980, pp. 93-106.

Woodward, S.C. et al., "Histotoxicity of Cyanoacrylate Tissue Adhesives in the Rat", Annals of Surgery, vol. 162, No. 1, Jul. 1965, pp. 113-122.

Yonezawa, M. et al., Studies on a-Cyanoacrylate, VI: Reaction of Cyanoacetate with Formaldehyde Yuki Gosei Kagaku Kyokaishi, vol. 25, Iss 4, Apr. 1967, pp. 311-316.

Simonova, G., et al., "Cyanoacrylate tissue adhesives-effective securement technique for intravascular catheters: in vitro testing safety and feasibility," Anaesthesia and Intensive Care, vol. 40, No. 3, May 2012, pp. 460-466.

Wilkinson, J.N., et al., "Securing epidural catheters with Histoacryl glue," Anaesthesia, 2008, 63, pp. 316-327.

Gurnaney, H., et al., "Dermabond Decreases Pericatheter Local Anesthetic Leakage After Continuous Perineural Infusions," Anesthesia & Analgesia, 2011, p. 206.

Wilkinson, J.N., et al., "Tissue adhesive as an alternative to sutures for securing central venous catheters", Anaesthesia, 2007, 62, pp. 966-974.

International Search Report and Written Opinion dated Dec. 8, 2010 for international application No. PCT/US2009/062761.

Schoonhoven, et al., "Incidence of pressure ulcers due to surgery", J. Clin. Nurs., Jul. 2002; 11(4):479-87 (Abstract Only).

* cited by examiner

STERILIZED LIQUID COMPOSITIONS OF CYANOACRYLATE MONOMER MIXTURES

CROSS REFERENCE TO RELATED APPLICATIONS

This application is a continuation-in-part of U.S. application Ser. No. 13/953,011 filed on Jul. 29, 2013, now U.S. Pat. No. 8,652,510 issued Feb. 18, 2014, which is a continuation-in-part of U.S. application Ser. No. 12/378,277 filed on Feb. 12, 2009, now U.S. Pat. No. 8,609,128 issued Dec. 17, 2013, and claims priority to U.S. Provisional Application No. 61/197,954 filed on Oct. 31, 2008. The contents of each application are incorporated by reference herein, in their entirety and for all purposes.

FIELD OF THE INVENTION

The invention relates generally to the field of medicinal cyanoacrylate chemistry. More particularly, the invention relates to low viscosity cyanoacrylate compositions that may be sterilized by irradiation with minimal post-sterilization viscosity changes, as well as methods for using compositions as medical sealant drapes and catheter anchors.

BACKGROUND OF THE INVENTION

Various publications, including patents, published applications, technical articles and scholarly articles are cited throughout the specification. Each cited publication is incorporated by reference herein, in its entirety and for all purposes.

Surgical site infections (SSIs) can be classified into two categories: (1) incisional and (2) organ, which includes organs and spaces manipulated during an operation. Incisional infections are further divided into superficial infections and deep soft tissue-muscle and fascia infections. The Centers for Disease Control and Prevention estimates that approximately 500,000 surgical site infections occur among an estimated 27 million surgical procedures conducted every year in the United States. Surgical site infections (SSI) are listed as the second most common cause of nosocomial infection after urinary tract infections, which accounts for 40% of hospital-acquired infections among surgical patients. Twenty five to thirty-eight percent of all nosocomial infections among surgical patients are estimated to be incisional surgical site infections. SSI is a significant cause of surgical morbidity and mortality, occurring in 2-5% of patients having clean extra-abdominal operations and up to 20% of patients undergoing intra-abdominal procedures. Patients with SSI are twice as likely to die, 60% more likely to be admitted to an Intensive Care Unit, and more than 5 times more likely to be readmitted to the hospital than patients who are not infected.

Surgical site infections result in longer hospitalization and have large economic impact on patients and the health care system. Patients with surgical site infections are hospitalized an additional 7 days on average. The longer hospital stay cost an additional $3,152 on average. The average total cost for medical care during the eight weeks after hospital discharge is $5,155 for patients with surgical site infections compared with $1,773 for patients without SSIs. The total cost includes outpatient visits, pharmacy, radiology services, re-hospitalization, skill-nursing facility, home health aides, and durable equipment.

Topical bactericidal active or antimicrobial agents such as iodophors, chlorhexidine, and alcohol-containing products have been applied to the surgical site before surgery to kill bacteria. These agents are preoperative skin preparation products, washes, surgical scrub tissues, wound cleaners, lotions and ointments. As early as 1960s, the successful use of prophylactic antibiotics was reported in a randomized, prospective, placebo-controlled clinical study of abdominal operations on the gastrointestinal tract. The success of antibiotic prophylaxis was due to the appropriate patient selection and wise choice of available agents.

One of the disadvantages associated with topical application of skin preparation products is that the antimicrobial agents are only effective for a short period of time. Bacteria that may have survived the initial application of skin preparation products can proliferate and produce a large pathogen population. In addition, appropriate antimicrobial prophylaxis is determined by many factors such as proper case selection, anti-microbial agent selection, dosing and route of administration and duration of therapy. Inappropriate use of antimicrobial agents not only increases the cost of medical health care, but also exposes the patient to potential toxicity and other risks. Moreover, many gram-positive organisms isolated from patients with surgical site infections are resistant to multiple antimicrobial agents. The problem of antimicrobial resistance in gram-positive nosocomial pathogens has been a growing concern.

In addition to the use of antimicrobial skin preparation products, surgical incise drapes have also been used to help reduce the migration of germs and bacteria into the incision site. The surgical incise drape is usually a clear polymeric film with an adhesive backing on one side which is in turn covered with a release liner. Generally, the incise drape is used in conjunction with towels or surgical drapes to maintain the surgical site as sterile and clean as possible in order to inhibit surgical site infections. A continuous or longer lasting antimicrobial effect may be obtained by combining the antimicrobial agent with a surgical incise drape.

In spite of the beneficial properties of conventional surgical drapes with respect to inhibition bacterial infection, there are many challenges and problems associated with the conventional surgical drapes regardless of whether they incorporate antimicrobial agents. Under certain circumstances conventional surgical drapes may actually increase the risk of surgical site infection. Conventional surgical drapes can be lifted during surgery which results in entry of bacteria into the surgical site. The lifting of the conventional surgical drape is usually caused by failure of the adhesive to remain in contact with the patient's skin. Attempts to increase adhesive strength may also prove disadvantageous because more force is then required to remove the drape from skin leading to damage of the skin near the surgical site.

Cyanoacrylate properties as adhesives may also make them desirable candidates as microbial sealant drapes. Cyanoacrylate microbial sealant drapes could prevent surgical site infections by overcoming the difficulties experienced by the conventional surgical drapes.

There are several shortcomings associated with using n-butyl cyanoacrylate as a surgical drape. Compared to longer chain alkyl cyanoacrylates, n-butyl cyanoacrylate is less flexible and cracks more easily after forming a polymer film. Thus a plasticizer is usually needed in the n-butyl cyanoacrylate formulation to improve flexibility. In addition, short-chain cyanoacrylates polymerize quickly and then degrade rapidly into formaldehyde and the corresponding alkyl cyanoacetate, which can cause significant histotoxicity. Relatedly, short chain cyanoacrylates such as n-butyl cyanoacrylate tend to polymerize quite readily, thereby substantially increasing in viscosity and even curing after exposure to irradiation. Polymer films of n-butyl cyanoacrylate sloughs off from skin faster than that of long alkyl chain cyanoacrylates. Skin irritation also occurs with the use of n-butyl cyanoacrylate.

Hence, development of a cyanoacrylate-based microbial sealant drape which can immobilize the infectious microorganisms and effectively seal out the bacteria from a surgical site is desired. It is desirable to have a cyanoacrylate-based microbial sealant drape product that can provide a uniform and flexible film. It is also desirable to develop a cyanoacrylate microbial sealant drape with significantly less tissue toxicity. Additionally, it is also desirable to develop an easy to use cyanoacrylate-based microbial sealant drape that will last a long time after the surgery to inhibit the postoperative surgical site infections.

SUMMARY OF THE INVENTION

The invention features liquid cyanoacrylate monomer-based adhesive compositions comprising stabilized and sterilized mixtures of cyanoacrylate monomers, which exhibit anti-microbial properties. The sealant film formed upon polymerization of the cyanoacrylate monomers also may prevents the spread of microorganisms such as bacteria by trapping and immobilizing them within the film. The compositions provide flexible microbial sealant drapes without the addition of plasticizers and/or antimicrobial agents.

A cyanoacrylate adhesive composition comprises a mixture of about 78% to about 82% by weight of monomeric 2-octyl cyanoacrylate, about 22% to about 18% by weight of monomeric n-butyl cyanoacrylate, about 2000 ppm to about 14,000 ppm of butylated hydroxyl anisole, and about 10 ppm to about 200 ppm of sulfur dioxide or about 5 ppm to about 50 ppm of an acid stabilizer selected from the group consisting of sulfuric acid, phosphoric acid, and perchloric acid. The composition may be sterilized by ethylene oxide or irradiation. Irradiation may comprise E-beam or gamma irradiation. Following sterilization, the viscosity of the composition increases no more than about 300%. The sterilized composition has at least two years of shelf storage stability. The two years of shelf storage stability may be measured in real time or according to an American Society for Testing and Materials (ASTM) accelerated aging standard. Shelf storage stability may comprise a minimal change in viscosity of the composition over a period of time.

In some preferred aspects, the cyanoacrylate adhesive composition comprises a mixture of about 79% to about 81% by weight of monomeric 2-octyl cyanoacrylate, about 21% to about 19% by weight of monomeric n-butyl cyanoacrylate, about 2000 ppm to about 14,000 ppm of butylated hydroxyl anisole, and about 10 ppm to about 200 ppm of sulfur dioxide. In some preferred aspects, the cyanoacrylate adhesive composition comprises a mixture of about 80% by weight of monomeric 2-octyl cyanoacrylate, about 20% by weight of monomeric n-butyl cyanoacrylate, about 2000 ppm to about 14,000 ppm of butylated hydroxyl anisole, and about 10 ppm to about 200 ppm of sulfur dioxide.

In some preferred aspects, the cyanoacrylate adhesive composition comprises a mixture of about 79% to about 81% by weight of monomeric 2-octyl cyanoacrylate, about 21% to about 19% by weight of monomeric n-butyl cyanoacrylate, about 2000 ppm to about 8000 ppm of butylated hydroxyl anisole, and about 10 ppm to about 200 ppm of sulfur dioxide. In some preferred aspects, the cyanoacrylate adhesive composition comprises a mixture of about 80% by weight of monomeric 2-octyl cyanoacrylate, about 20% by weight of monomeric n-butyl cyanoacrylate, about 2000 ppm to about 8000 ppm of butylated hydroxyl anisole, and about 10 ppm to about 200 ppm of sulfur dioxide.

In some preferred aspects, a cyanoacrylate adhesive composition comprises a mixture of about 80% by weight of monomeric 2-octyl cyanoacrylate, about 20% by weight of monomeric n-butyl cyanoacrylate, about 2000 ppm to about 14,000 ppm of butylated hydroxyl anisole, and about 10 ppm to about 200 ppm of sulfur dioxide, and is sterilized by gamma irradiation or electron beam irradiation. The viscosity of the composition preferably does not increase more than about 300% after sterilization, and the sterilized composition preferably has at least two years of shelf storage stability. The composition preferably does not include any plasticizer, and in some aspects also does not include any antimicrobial agent.

The ASTM accelerated aging standard may comprise the ASTM F1980-02 standard. The ASTM accelerated aging standard may comprise the ASTM F1980-07 standard.

The composition may further comprise a polymerization accelerator. The polymerization accelerator is preferably a crown ether polymerization accelerator, and more preferably is 18-crown-6 crown ether. The polymerization accelerator may comprise about 10 ppm to about 150 ppm. The polymerization accelerator may comprise about 50 ppm to about 100 ppm.

In some aspects, the viscosity of the sterilized composition increases no more than about 300% after about one year of shelf storage. In some aspects, the viscosity of the sterilized composition increases no more than about 250% after about one year of shelf storage. In some aspects, the viscosity of the sterilized composition increases no more than about 200% after about one year of shelf storage. In some aspects, the viscosity of the sterilized composition increases no more than about 300% after about two years of shelf storage. In some aspects, the viscosity of the sterilized composition increases no more than about 250% after about two years of shelf storage. In some aspects, the viscosity of the sterilized composition increases no more than about 200% after about two years of shelf storage.

The invention also features methods for closing a wound, which may be a trauma wound or a surgical wound, or may be a skin ulcer, including a pressure ulcer and including a bed sore. The methods may comprise applying a cyanoacrylate adhesive composition comprising a mixture of about 78% to about 82% by weight of monomeric 2-octyl cyanoacrylate, about 22% to about 18% by weight of monomeric n-butyl cyanoacrylate, about 2000 ppm to about 14,000 ppm of butylated hydroxyl anisole, and about 10 ppm to about 200 ppm of sulfur dioxide or about 5 ppm to about 50 ppm of an acid stabilizer selected from the group consisting of sulfuric acid, phosphoric acid, and perchloric acid to the wound and allowing the composition to cure over the wound, thereby closing the wound. The composition is preferably sterilized by ethylene oxide, or by irradiation such as gamma or E-beam radiation. In some preferred aspects, the cyanoacrylate adhesive composition comprises a mixture of about 79% to about 81% by weight of monomeric 2-octyl cyanoacrylate, about 21% to about 19% by weight of monomeric n-butyl cyanoacrylate, about 2000 ppm to about 14,000 ppm of butylated hydroxyl anisole, and about 10 ppm to about 200 ppm of sulfur dioxide. In some preferred aspects, the cyanoacrylate adhesive composition comprises a mixture of about 80% by weight of monomeric 2-octyl cyanoacrylate, about 20% by weight of monomeric n-butyl cyanoacrylate, about 2000 ppm to about 14,000 ppm of butylated hydroxyl anisole, and about 10 ppm to about 200 ppm of sulfur dioxide.

The methods may comprise applying a cyanoacrylate adhesive composition comprising a mixture of about 78% to about 82% by weight of monomeric 2-octyl cyanoacrylate, about 22% to about 18% by weight of monomeric n-butyl cyanoacrylate, about 2000 ppm to about 8000 ppm of butylated hydroxyl anisole, and about 10 ppm to about 200 ppm of sulfur dioxide or about 5 ppm to about 50 ppm of an acid stabilizer selected from the group consisting of sulfuric acid, phosphoric acid, and perchloric acid to the wound and allowing the composition to cure over the wound, thereby closing the wound. The composition is preferably sterilized by ethylene oxide, or by irradiation such as gamma or E-beam radiation. In some preferred aspects, the cyanoacrylate adhesive composition comprises a mixture of about 79% to about 81% by weight of monomeric 2-octyl cyanoacrylate, about 21% to about 19% by weight of monomeric n-butyl cyanoacrylate, about 2000 ppm to about 8000 ppm of butylated hydroxyl anisole, and about 10 ppm to about 200 ppm of sulfur dioxide. In some preferred aspects, the cyanoacrylate adhesive composition comprises a mixture of about 80% by weight of monomeric 2-octyl cyanoacrylate, about 20% by weight of monomeric n-butyl cyanoacrylate, about 2000 ppm to about 8000 ppm of butylated hydroxyl anisole, and about 10 ppm to about 200 ppm of sulfur dioxide.

The invention also features methods for securing a catheter in place, which catheter has been inserted into the body of a subject, and is to be secured in place where inserted. The methods may comprise applying a cyanoacrylate adhesive composition comprising a mixture of about 78% to about 82% by weight of monomeric 2-octyl cyanoacrylate, about 22% to about 18% by weight of monomeric n-butyl cyanoacrylate, about 2000 ppm to about 14,000 ppm of butylated hydroxyl anisole, and about 10 ppm to about 200 ppm of sulfur dioxide or about 5 ppm to about 50 ppm of an acid stabilizer selected from the group consisting of sulfuric acid, phosphoric acid, and perchloric acid to a surface of the body and to a surface on the catheter and allowing the composition to cure between the surface of the body and the surface on the catheter, thereby securing the catheter in place. The composition is preferably sterilized by ethylene oxide, or by irradiation such as gamma or E-beam radiation. In some preferred aspects, the cyanoacrylate adhesive composition comprises a mixture of about 79% to about 81% by weight of monomeric 2-octyl cyanoacrylate, about 21% to about 19% by weight of monomeric n-butyl cyanoacrylate, about 2000 ppm to about 14,000 ppm of butylated hydroxyl anisole, and about 10 ppm to about 200 ppm of sulfur dioxide. In some preferred aspects, the cyanoacrylate adhesive composition comprises a mixture of about 80% by weight of monomeric 2-octyl cyanoacrylate, about 20% by weight of monomeric n-butyl cyanoacrylate, about 2000 ppm to about 14,000 ppm of butylated hydroxyl anisole, and about 10 ppm to about 200 ppm of sulfur dioxide.

The methods comprise applying a cyanoacrylate adhesive composition comprising a mixture of about 78% to about 82% by weight of monomeric 2-octyl cyanoacrylate, about 22% to about 18% by weight of monomeric n-butyl cyanoacrylate, about 2000 ppm to about 8000 ppm of butylated hydroxyl anisole, and about 10 ppm to about 200 ppm of sulfur dioxide or about 5 ppm to about 50 ppm of an acid stabilizer selected from the group consisting of sulfuric acid, phosphoric acid, and perchloric acid to a surface of the body and to a surface on the catheter and allowing the composition to cure between the surface of the body and the surface on the catheter, thereby securing the catheter in place. The composition is preferably sterilized by ethylene oxide, or by irradiation such as gamma or E-beam radiation. In some preferred aspects, the cyanoacrylate adhesive composition comprises a mixture of about 79% to about 81% by weight of monomeric 2-octyl cyanoacrylate, about 21% to about 19% by weight of monomeric n-butyl cyanoacrylate, about 2000 ppm to about 8000 ppm of butylated hydroxyl anisole, and about 10 ppm to about 200 ppm of sulfur dioxide. In some preferred aspects, the cyanoacrylate adhesive composition comprises a mixture of about 80% by weight of monomeric 2-octyl cyanoacrylate, about 20% by weight of monomeric n-butyl cyanoacrylate, about 2000 ppm to about 8000 ppm of butylated hydroxyl anisole, and about 10 ppm to about 200 ppm of sulfur dioxide.

DETAILED DESCRIPTION OF THE INVENTION

Various terms relating to aspects of the invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

It has been observed in accordance with the invention that certain alpha cyanoacrylate monomers can be mixed together in certain ratios and stabilized as a composition such that the composition can be sterilized without the sterilization significantly inducing polymerization of the monomers or inducing curing of the composition. It has also been observed that such sterilized compositions remain shelf stable over time—without significant polymerization of the monomers or curing of the composition during shelf storage. It has also been observed that such sterilized compositions have anti-bacterial properties, and may inhibit the growth of bacteria on wounds to which such compositions are applied. Accordingly, in one aspect, the invention features sterilized cyanoacrylate monomer compositions.

The compositions include at least two cyanoacrylate monomers. One of the two cyanoacrylate monomers comprises at least five carbon atoms in the alkyl group, including but not limited to n-pentyl cyanoacrylate, iso-pentyl cyanoacrylate, n-hexyl cyanoacrylate, iso-hexyl cyanoacrylate, n-heptyl cyanoacrylate, 2-ethylhexyl cyanoacrylate, n-octyl cyanoacrylate, 2-octyl cyanoacrylate, nonyl cyanoacrylate, and decyl cyanoacrylate. The other of the two cyanoacrylate monomers comprises four or fewer carbon atoms in the alkyl group, including but not limited to methyl cyanoacrylate, ethyl cyanoacrylate, n-propyl cyanoacrylate, isopropyl cyanoacrylate, n-butyl cyanoacrylate, isobutyl cyanoacrylate, 3-acetoxypropyl cyanoacrylate, 2-methoxypropyl cyanoacrylate, and 3-chloropropyl cyanoacrylate.

Varying the ratio of each cyanoacrylate monomer varies certain properties of the resultant cyanoacrylate compositions, including bonding strength, flexibility, cure time, degradability, and biocompatibility. Cyanoacrylate monomers comprising five or more alkyl chains lacking oxygen-containing functional groups tend to form polymers that degrade slowly. Compared to such longer chain cyanoacrylates, cyanoacrylate monomers with four or fewer alkyl chains have a higher degree of tissue toxicity due to their rapid degradation into formaldehyde and the corresponding cyanoacetate. Polymer films comprising longer (five or more carbons) alkyl chain cyanoacrylate tend to be more flexible than those made of shorter (four or fewer carbons) alkyl chain cyanoacrylates. Shorter alkyl chain cyanoacrylates have advantageous properties as tissue adhesives. For example, shorter alkyl chain cyanoacrylates provide faster curing speed and stronger bond strength as compared to longer alkyl chain cyanoacrylates.

Highly preferred compositions comprise 2-octylcyanoacrylate (OCA) in combination with n-butyl cyanoacrylate (BCA). These compositions comprise any weight percentage ratio of OCA to BCA suitable for withstanding sterilization, particularly radiation-based sterilization, without increasing the viscosity of the composition to levels unsuitable for a liquid adhesive after sterilization, even for extended periods of time after sterilization.

The compositions may comprise a cyanoacrylate monomer adhesive comprising OCA and BCA in an OCA to BCA weight percentage ratio of about 60 to about 40, about 65 to about 35, about 70 to about 30, about 72 to about 28, about 74 to about 26, about 76 to about 24, about 78 to about 22, about 80 to about 20, about 82 to about 18, about 84 to about 16, about 86 to about 14, about 88 to about 12, about 90 to about 10, about 92 to about 8, or about 94 to about 6. The OCA may comprise about 75 to about 85 percent, by weight, of the cyanoacrylate monomer adhesive and the BCA may comprise about 15 to about 25 percent, by weight, of the cyanoacrylate monomer adhesive. The OCA may comprise about 76 to about 84 percent, by weight, of the cyanoacrylate monomer adhesive and the BCA may comprise about 16 to about 24 percent, by weight, of the cyanoacrylate monomer adhesive. The OCA may comprise about 77 to about 83 percent, by weight, of the cyanoacrylate monomer adhesive and the BCA may comprise about 17 to about 23 percent, by weight, of the cyanoacrylate monomer adhesive. The OCA may comprise about 78 to about 82 percent, by weight, of the cyanoacrylate monomer adhesive and the BCA may comprise about 18 to about 22 percent, by weight, of the cyanoacrylate monomer adhesive. The OCA may comprise about 79 to about 81 percent, by weight, of the cyanoacrylate monomer adhesive and the BCA may comprise about 19 to about 21 percent, by weight, of the cyanoacrylate monomer adhesive. In highly preferred aspects, the OCA may comprise about 80 percent, by weight, of the cyanoacrylate monomer adhesive and the BCA may comprise about 20 percent, by weight, of the cyanoacrylate monomer adhesive.

The cyanoacrylate compositions preferably include stabilizing agents that stabilize the cyanoacrylate monomer mixture. The compositions may be stabilized with a combination of a free radical stabilizer and an anionic stabilizer. Free radical stabilizers that may be used include without limitation, hydroquinone; catechol; hydroquinone monomethyl ether and hindered phenols such as butylated hydroxyanisol; 4-ethoxyphenol; butylated hydroxytoluene (BHT, 2,6-di-tert-butyl butylphenol), 4-methoxyphenol (MP); 3-methoxyphenol; 2-tert-butyl-4-methoxyphenol; 2,2-methylene-bis-(4-methyl-6-tert-butylphenol). In preferred aspects, the free radical stabilizer is butylated hydroxyl anisole (BHA).

The free radical stabilizer may be used in an amount effective to stabilize the cyanoacrylate monomers such that the monomers do not substantially polymerize prematurely, either before or after sterilization and any subsequent shelf storage. A free radical stabilizer such as BHA may comprise about 200 ppm to about 15,000 ppm of the composition. The free radical stabilizer may comprise about 1000 ppm to about 15,000 ppm, about 2000 ppm to about 15,000 ppm of the composition, or about 3000 ppm to about 14,000 ppm. A free radical stabilizer such as BHA may comprise about 2000 ppm to about 14,000 ppm of the composition. The free radical stabilizer may comprise about 2000 ppm to about 10,000 ppm, about 2000 ppm to about 15,000 ppm of the composition, or about 2000 ppm to about 8000 ppm.

Anionic stabilizers that may be used include sulfur dioxide, and also include strong acids such as perchloric acid, hydrochloric acid, hydrobromic acid, toluenesulfonic acid, fluorosulfonic acid, phosphoric acid, ortho, meta, or para-phosphoric acid, trichloroacetic acid, and sulfuric acid. Generally speaking, the compositions comprise either sulfur dioxide or a strong acid anionic stabilizer, but not both, although both may be used in some aspects. When sulfur dioxide is used, the sulfur dioxide may comprise about 2 to about 500 ppm, about 5 to about 300 ppm, about 10 ppm to about 200 ppm, or about 5 ppm to about 50 ppm. When a strong acid is used, the strong acid may comprise about 1 ppm to about 250 ppm, about 3 ppm to about 150 ppm, about 4 ppm to about 100 ppm, about 5 ppm to about 50 ppm, about 10 ppm to about 40 ppm, about 20 ppm to about 40 ppm, or about 30 ppm to about 40 ppm.

In some preferred aspects, a composition comprises a cyanoacrylate monomer adhesive comprising about 78 to about 82 percent by weight of OCA and about 18 to about 22 percent by weight of BCA, and comprising about 2000 ppm to about 14,000 ppm of a free radical stabilizer, and about 10 ppm to about 200 ppm of sulfur dioxide or about 5 ppm to about 50 ppm of an anionic stabilizer. In some preferred aspects, a composition comprises a cyanoacrylate monomer adhesive comprising about 79 to about 81 percent by weight of OCA and about 19 to about 21 percent by weight of BCA, and comprising about 2000 ppm to about 14,000 ppm of a free radical stabilizer, and about 10 ppm to about 200 ppm of sulfur dioxide or about 5 ppm to about 50 ppm of an anionic stabilizer. In some preferred aspects, a composition comprises a cyanoacrylate monomer adhesive comprising about 80 percent by weight of OCA and about 20 percent by weight of BCA, and comprising about 2000 ppm to about 14,000 ppm of a free radical stabilizer, and about 10 ppm to about 200 ppm of sulfur dioxide or about 5 ppm to about 50 ppm of an anionic stabilizer.

In some preferred aspects, a composition comprises a cyanoacrylate monomer adhesive comprising about 78 to about 82 percent by weight of OCA and about 18 to about 22 percent by weight of BCA, and comprising about 2000 ppm to about 8000 ppm of a free radical stabilizer, and about 10 ppm to about 200 ppm of sulfur dioxide or about 5 ppm to about 50 ppm of an anionic stabilizer. In some preferred aspects, a composition comprises a cyanoacrylate monomer adhesive comprising about 79 to about 81 percent by weight of OCA and about 19 to about 21 percent by weight of BCA, and comprising about 2000 ppm to about 8000 ppm of a free radical stabilizer, and about 10 ppm to about 200 ppm of sulfur dioxide or about 5 ppm to about 50 ppm of an anionic stabilizer. In some preferred aspects, a composition comprises a cyanoacrylate monomer adhesive comprising about 80 percent by weight of OCA and about 20 percent by weight of BCA, and comprising about 2000 ppm to about 8000 ppm of a free radical stabilizer, and about 10 ppm to about 200 ppm of sulfur dioxide or about 5 ppm to about 50 ppm of an anionic stabilizer.

The compositions may comprise a polymerization accelerator. The polymerization accelerator may comprise calixarenes and oxacalixarenes, silacrowns, crown ethers, including 18-crown-6 crown ether, cyclodextrin and its derivatives, polyethers, aliphatic alcohol, aliphatic carboxylic acid esters, benzoyl peroxide, triethyl amine, diethyl amine, butyl amine, isopropyl amine, tributyl amine, N,N-dimethyl aniline, N,N-diethyl aniline, N,N-dimethyl-p-toluidine, N,N-dimethyl-m-toluidine, N,N-dimethyl-o-toluidine, dimethyl benzyl amine, pyridine, picoline, vinyl pyridine, ethanolamine, propanolamine and ethylene diamine, quaternary ammonium salts such as alkyl ammonium salts, amide-bonded ammonium salts, ester-bonded ammonium salts such as alkylammonium salts, amide-bonded ammonium salts, ester-bonded ammonium salts, salts and alkylimidazolinium salts, cyclosulfur compounds and derivatives, and polyalkylene oxides and derivatives thereof. The polymerization accelerator may comprise about 5 ppm to about 250 ppm of the composition, more preferably about 5 ppm to about 200 ppm, more preferably about 5 ppm to about 150 ppm, and more preferably about 10 ppm to about 150 ppm.

The cyanoacrylate compositions are preferably sterilized for medical use. The sterilization can be accomplished by any suitable techniques, and is preferably accomplished by chemical (e.g., ethylene oxide), physical (e.g., dry heat), or irradiation. Irradiation may comprise gamma irradiation, electron beam irradiation (E-beam), microwave irradiation, X-ray irradiation, or combinations thereof. E-beam irradiation and gamma irradiation are preferred for sterilizing the compositions.

In some preferred aspects, E-beam irradiation is used to sterilize the cyanoacrylate compositions. The dose of E-beam irradiation applied should be sufficient enough to sterilize the composition and any container or packaging in which the composition is housed. The E-beam irradiation may be in a dosage of about 5 kGy to 50 kGy, and more preferably about 12 kGy to about 25 kGy. E-beam irradiation is preferably conducted at ambient atmosphere conditions and the exposure time to the irradiation is preferably from about 1 to about 60 seconds, more preferably from about 10 seconds to 60 seconds. Any standard power source is suitable, including a linear accelerator, which produces irradiation measured in kilo watts (KW). The larger the beam power, the more product volume can be processed. The cyanoacrylate adhesive compositions may be irradiated at a beam power of about 2 KW to about 30 KW, preferably about 5 KW to about 20 KW, and more preferably about 10 KW to about 20 KW. E-beam irradiation typically involves the use of high-energy electrons. The beam energy generally ranges from about 1 million to about 10 million electron volts (MeV), preferably about 3 MeV to about 10 MeV, and more preferably about 5 MeV to about 10 MeV.

In some preferred aspects, gamma irradiation is used to sterilize the cyanoacrylate compositions. A standard Cobalt Co-60 may be used as the gamma ray source in sterilizing the compositions. The dose of gamma irradiation applied should be sufficient enough to sterilize the composition and any container or packaging in which the composition is housed. The gamma irradiation may be in a dosage of about 5 kGy to 50 kGy, more preferably about 5 kGy to about 30 kGy, more preferably about 5 kGy to about 25 kGy, and more preferably about 5 kGy to about 20 kGy. In some aspects, gamma irradiation may be in a dosage of about 10 kGy to about 15 kGy. Gamma irradiation is preferably conducted at a temperature of about 20 degrees C. to about 65 degrees C., or about 25 degrees C. to about 60 degrees C., or about 25 degrees C. to about 50 degrees C., and the exposure time to the irradiation is preferably from about 1 minute to about 80 minutes, more preferably about 10 minutes to about 100 minutes, and more preferably from about 10 minutes to about 70 minutes.

Before sterilization, the composition preferably has a viscosity of about 2 to about 10 cps. In some aspects, the composition has a pre-sterilization viscosity of about 2.5 to about 7.5 cps. In some aspects, the composition has a pre-sterilization viscosity of about 3 to about 7 cps. In some aspects, the composition has a pre-sterilization viscosity of about 3 to about 6.5 cps. In some aspects, the composition has a pre-sterilization viscosity of about 3 to about 6 cps. In some aspects, the composition has a pre-sterilization viscosity of about 3 to about 5 cps. In some aspects, the composition has a pre-sterilization viscosity of about 3.5 to about 7 cps. In some aspects, the composition has a pre-sterilization viscosity of about 3.5 to about 6.5 cps. In some aspects, the composition has a pre-sterilization viscosity of about 3.5 to about 6 cps.

It was observed that for some compositions comprising 20% butyl cyanoacrylate and 80% octyl cyanoacrylate, the average viscosity of the before sterilization was about 4.1 cps. After the sealant composition was placed into an applicator and subjected to E-beam sterilization, the average viscosity was observed to decrease to about 3.7 cps.

In order to investigate the stability of the mixture of 2-octyl cyanoacrylate and n-butyl cyanoacrylate, a series of mixed cyanoacrylate compositions with different ratio of OCA/BCA were prepared and subjected to sterilization. The compositions tested included the following ratios of n-butyl cyanoacrylate to 2-octyl cyanoacrylate: 10:90, 20:80, 30:70, 40:60, 50:50, 60:40, 70:30, 80:20 and 90:10. Table 1 shows the viscosity of the 2-octyl cyanoacrylate and n-butyl cyanoacrylate mixtures before and after the E-beam sterilization. As shown in Table 1, E-beam sterilization had different effects on different mixtures of 2-octyl cyanoacrylate and n-butyl cyanoacrylate depending on the ratio of the two cyanoacrylates. The viscosity of the different compositions of Table 1 before the sterilization ranged from 3.68 to 3.88 cps. Mixed cyanoacrylate compositions having approximately 60% to about 90% 2-octyl cyanoacrylate demonstrated slight viscosity increases after E-beam sterilization.

TABLE 1

Viscosity of mixed OCA/BCA compositions before and after E-beam sterilization.

| | | Average viscosity (cps) | |
|---|---|---|---|
| Formulation | Composition | Before Sterilization | After Sterilization |
| 1a | 1:9 BCA/OCA | 3.68 | 5.11 |
| 1b | 2:8 BCA/OCA | 3.68 | 5.71 |
| 1c | 3:7 BCA/OCA | 3.68 | 5.11 |
| 1d | 4:6 BCA/OCA | 3.88 | 6.95 |
| 1e | 5:5 BCA/OCA | 3.88 | 15.77 |
| 1f | 6:4 BCA/OCA | 3.88 | 68.03 |
| 1g | 7:3 BCA/OCA | 3.68 | 505.63 |
| 1h | 8:2 BCA/OCA | 3.68 | Cured |
| 1i | 9:1 BCA/OCA | 3.68 | Cured |

Following sterilization, the viscosity of the composition preferably does not increase more than about 400% of the pre-sterilization viscosity. Following sterilization, the viscosity of the composition preferably does not increase more than about 350% of the pre-sterilization viscosity. Following sterilization, the viscosity of the composition preferably does not increase more than about 300% of the pre-sterilization viscosity. Following sterilization, the viscosity of the composition preferably does not increase more than about 250% of the pre-sterilization viscosity. Following sterilization, the viscosity of the composition preferably does not increase more than about 200% of the pre-sterilization viscosity. Following sterilization, the viscosity of the composition preferably does not increase more than about 150% of the pre-sterilization viscosity. Following sterilization, the viscosity of the composition preferably does not increase more than about 100% of the pre-sterilization viscosity. Sterilization may be according to any suitable method, including chemical or irradiation as described or exemplified herein.

It is preferred that the compositions provide at least one year, and more preferably two-years of shelf life. Shelf life is, in part, reflected in post-sterilization viscosity changes. For example, the post-sterilization viscosity changes described herein may be measured at least about six months, at least about one year, at least about one and one half years, or at least about two years following sterilization. The period of time as measured may elapse in real time, or may be approximated via an accelerated aging study. The American Society for Testing and Materials (ASTM) has established standard advance aging assays for investigating the aging of sterilized medical device packages. One such standard is the ASTM F1980-02 Standard Guide for Accelerated Aging of Sterile Medical Device Packages. The F1980-02 standard has been superseded by the ASTM F1980-07 (2011) Standard Guide for Accelerated Aging of Sterile Barrier Systems for Medical Devices. Either standard accelerated aging test may be used to approximate two years of real time aging of the compositions. In general, the compositions undergoing an accelerated aging test are warehoused in an oven at 80° C. (dry heat) for a period of 12 days (F1980-02) or for a period of 13 days (F1980-07), which respectively approximate two years of shelf life at ordinary storage temperatures and atmospheric conditions. In some aspects, the compositions undergoing an accelerated aging test are warehoused in an oven at 80° C. (dry heat) for a period of 6 days (F1980-02) or for a period of 6.5 days (F1980-07), which respectively approximate one year of shelf life at ordinary storage temperatures and atmospheric conditions.

During shelf storage, the sterilized compositions may further change in viscosity. The viscosity may increase or decrease, although the viscosity may tend to increase.

Following about one year of shelf storage, the viscosity of the sterilized composition preferably does not increase more than about 600% of the pre-sterilization viscosity. Following about one year of shelf storage, the viscosity of the sterilized composition preferably does not increase more than about 500% of the pre-sterilization viscosity. Following about one year of shelf storage, the viscosity of the sterilized composition preferably does not increase more than about 450% of the pre-sterilization viscosity. Following about one year of shelf storage, the viscosity of the sterilized composition preferably does not increase more than about 400% of the pre-sterilization viscosity. Following about one year of shelf storage, the viscosity of the sterilized composition preferably does not increase more than about 350% of the pre-sterilization viscosity. Following about one year of shelf storage, the viscosity of the sterilized composition preferably does not increase more than about 300% of the pre-sterilization viscosity. Following about one year of shelf storage, the viscosity of the sterilized composition preferably does not increase more than about 250% of the pre-sterilization viscosity. Following about one year of shelf storage, the viscosity of the sterilized composition preferably does not increase more than about 200% of the pre-sterilization viscosity. Following about one year of shelf storage, the viscosity of the sterilized composition preferably does not increase more than about 150% of the pre-sterilization viscosity.

Following about two years of shelf storage, the viscosity of the sterilized composition preferably does not increase more than about 1000% of the pre-sterilization viscosity. Following about two years of shelf storage, the viscosity of the sterilized composition preferably does not increase more than about 950% of the pre-sterilization viscosity. Following about two years of shelf storage, the viscosity of the sterilized composition preferably does not increase more than about 900% of the pre-sterilization viscosity. Following about two years of shelf storage, the viscosity of the sterilized composition preferably does not increase more than about 850% of the pre-sterilization viscosity. Following about two years of shelf storage, the viscosity of the sterilized composition preferably does not increase more than about 800% of the pre-sterilization viscosity. Following about two years of shelf storage, the viscosity of the sterilized composition preferably does not increase more than about 750% of the pre-sterilization viscosity. Following about two years of shelf storage, the viscosity of the sterilized composition preferably does not increase more than about 700% of the pre-sterilization viscosity. Following about two years of shelf storage, the viscosity of the sterilized composition preferably does not increase more than about 600% of the pre-sterilization viscosity. Following about two years of shelf storage, the viscosity of the sterilized composition preferably does not increase more than about 500% of the pre-sterilization viscosity. Following about two years of shelf storage, the viscosity of the sterilized composition preferably does not increase more than about 450% of the pre-sterilization viscosity. Following about two years of shelf storage, the viscosity of the sterilized composition preferably does not increase more than about 400% of the pre-sterilization viscosity. Following about two years of shelf storage, the viscosity of the sterilized composition preferably does not increase more than about 350% of the pre-sterilization viscosity. Following about two years of shelf storage, the viscosity of the sterilized composition preferably does not increase more than about 300% of the pre-sterilization viscosity. Following about two years of shelf storage, the viscosity of the sterilized composition preferably does not increase more than about 250% of the pre-sterilization viscosity. Following about two years of shelf storage, the viscosity of the sterilized composition preferably does not increase more than about 200% of the pre-sterilization viscosity.

Table 2 shows the viscosity of a sterilized composition of 80% OCA and 20% BCA packaged in a container and subject to advanced aging according to the ASTM F1980-02 standard twelve days at 80° C. The viscosity of the composition was measured on days 3, 4, 9, and 12 following sterilization, with day 0 representing viscosity measured after the sterilization was completed and before the accelerated aging study commenced. The test was run in triplicate (Tests 1-3). The viscosity of the compositions was observed to increase as the accelerated aging advanced, but the increased viscosity of the aged samples at day 12 did not affect the performance of composition (e.g., flowability and set time, not shown) nor the dispensing of the compositions from the applicator in which they were packaged.

TABLE 2

Viscosity of the sterile microbial sealant drape composition before and after the accelerated aging at 80° C. for 12 days.

| | Viscosity (cps) | | | |
|---|---|---|---|---|
| | Test 1 | Test 2 | Test 3 | Average |
| Day 0 | 4.29 | 3.68 | 3.06 | 3.68 |
| Day 3 | 4.29 | 3.68 | 4.90 | 4.29 |
| Day 6 | 4.90 | 4.90 | 5.52 | 5.11 |
| Day 9 | 6.13 | 6.13 | 6.74 | 6.33 |
| Day 12 | 27.0 | 25.7 | 30.6 | 27.8 |

The compositions may be used, for example, to close wounds. The wounds may be from a surgical incision, or may be from trauma, or may be a skin ulcer. For example, the compositions may be applied to the surface of the skin surrounding the wound and allowed to cure in place, thereby forming a film that surrounds the wound and bridges the injured tissue together. Accordingly, the invention features methods for closing a wound on a subject in need thereof. The subject may be any animal, with mammals being preferred. Mammals include farm animals, zoo animals, companion animals, and lab animals, and preferably include non-human primates. Human beings are highly preferred subjects.

In some aspects, methods for closing a wound comprise applying a cyanoacrylate monomer adhesive composition, including any such composition described or exemplified herein, to a wound and allowing the composition to polymerize on the wound such that the wound is thereby closed. Polymerization may culminate in curing of the composition when most or substantially all of the cyanoacrylate monomers polymerize together. The compositions preferably react with moisture on the skin surface, which moisture initiates the polymerization reaction without the need for any external polymerization initiation source. In some aspects, the wound may be held closed, for example, by the practitioner squeezing the sides of the wound together by hand or with a clamp or tool, until the composition sufficiently polymerizes or cures such that the polymerized film holds the wound closed without external help. In some aspects, the wound may be closed, at least in part, with stitches or with adhesive strips, and the composition applied over the stitches or strips to complete the wound closure. For example, for deep wounds, stitches may be used to bridge the internal tissue together and the compositions may be used to close the wound at the skin surface.

The compositions may be used, for example, to secure a catheter in place. For example, when a catheter is inserted into the body of a subject, the compositions may be used to secure the catheter in place, thereby preventing premature or unintentional removal or dislodging of the catheter. Accordingly, the invention features methods for securing a catheter on a subject in need thereof. The subject may be any animal, with mammals being preferred. Mammals include farm animals, zoo animals, companion animals, and lab animals, and preferably include non-human primates. Human beings are highly preferred subjects.

In some aspects, methods for securing a catheter comprise applying a cyanoacrylate monomer adhesive composition, including any such composition described or exemplified herein, to a surface of the catheter and a surface of the body and allowing the composition to polymerize between the catheter and the surface such that the catheter is thereby held in place. For example, the composition may be applied to a surface of the body, and thereafter, the catheter surface may be pushed into the composition bolus on the body surface and held in place until the composition polymerizes, or the composition may be applied to a surface of the catheter, and thereafter, the composition-containing catheter surface may be brought in contact with the body surface and held in place until the composition polymerizes, or the composition may be applied to both a surface of the catheter and a surface of the body, with each bolus of composition brought into contact with the other and the catheter held in place until the composition polymerizes. The body surface preferably comprises skin. The catheter may be any catheter inserted into the body as part of a medical procedure, including but not limited to an intravascular catheter, an epidural catheter, and an intravenous catheter. The compositions may be used to supplement, or used in lieu of adhesive tapes that are ordinarily used to secure catheters in place. When applied at or near the point of entry of the catheter into the body, the compositions may also close the wound caused by catheter insertion.

The compositions may be used, for example, to close or otherwise treat skin ulcers, including pressure ulcers such as bed sores. For example, the compositions may be applied to a skin ulcer, and allowed to cure on the skin ulcer, including a pressure ulcer such as a bed sore. The cured composition may remain on the skin ulcer for a period of time sufficient to close or otherwise treat the skin ulcer, including a pressure ulcer such as a bed sore. The application of the composition to a skin ulcer may be repeated multiple times (e.g., re-application) until the skin ulcer, including a pressure ulcer such as a bed sore, is healed or at least substantially healed. The compositions may inhibit progression of an early stage skin ulcer into a later, more severe stage skin ulcer. Accordingly, the invention features methods for closing skin ulcers, including pressure ulcers such as bed sores on a subject in need thereof, which comprise applying any cyanoacrylate composition described or exemplified herein onto the skin ulcer, and allowing the composition to cure on the skin ulcer. Maintaining contact between the cured composition and the skin ulcer closes the ulcer, and permits the body to heal the ulcer. The method may include the step of repeating the application of the composition after a period of time, for example, after about a day, or after about 2 days, or after about 3 days. The period of time is not critical, and may depend, for example, on when and the extent to which the cured composition from the previous application has degraded or otherwise lost its bonding strength or integrity. The subject may be any animal, with mammals being preferred. Mammals include farm animals, zoo animals, companion animals, and lab animals, and preferably include non-human primates. Human beings are highly preferred subjects.

The compositions may reduce the amount of microorganisms in or around a wound to which they are applied in order to adhere the tissue surrounding the wound together. The wound may comprise a catheter entrance or insertion wound. The wound may comprise a skin ulcer, and the skin ulcer may comprise a pressure ulcer such as a bed sore. In preferred embodiments, the compositions are also effective in preventing the spread of the pathogens such as bacteria beyond the footprint of the cured adhesive on the wound. As shown in the Examples below, the in vitro immobilization of microorganisms by the microbial sealant compositions was evaluated using sterile pig skin incised with a sterile surgical scalpel. Microorganisms used to challenge the surgical site may include without limitation pathogenic gram negative bacteria, gram positive bacteria, yeast and *Corynebacterium* sp. The immobilization of microorganisms by the compositions of the invention was evaluated under different conditions which included without limitation using the microbial sealant composition without incision, using the microbial sealant composition with incision, using the microbial sealant composition with incision and skin surgical preps, and using the microbial sealant composition with incision and surgical incise drapes.

The compositions were observed to be effective in preventing the mitigation in the test organism on the surgical site. Complete effectiveness was manifest as greater than 3.9 log 10 mitigation in the case of *S. epidermidis*, MRSA, *Corynebacterium* species, *Pseudomonas aeruginosa* and greater than 4 log 10 mitigation for *Candida albicans*. The compositions do not have an adverse effect on the effectiveness of surgical preps. The compositions preferably do not need to be used in combination with an antimicrobial surgical incise drape; instead, the compositions may be used as a substitute for an antimicrobial surgical incise drape. In some preferred aspects, the compositions do not include any antimicrobial agent.

In some aspects, the compositions can reduce microbial colonization by at least 99.9% within 15 minutes of application and maintain at least a 99.9% reduction throughout the 24 hours post-treatment.

In some aspects, the compositions are resistant to the passage of blood-borne pathogens. Testing based on ASTM F1671 "Test Method for Resistance of Materials Used in Protective Clothing to Penetration by Blood-Borne Pathogens Using Phi-X174 Bacteriophage Penetration as a Test System" was conducted to demonstrate the pathogen resistance. The test results indicated that the film produced by curing the compositions is resistant to the passage of blood-borne pathogens using a viral penetration as a test system.

It has been observed that the compositions generate less heat during the application compared to other compositions, including commercially available medical adhesives and drape products. The polymerization of cyanoacrylate monomers is an exothermic process, and the amount of heat released during polymerization is related to the length of the alkyl chain of the cyanoacrylate. Cyanoacrylates with shorter length chains release more heat. Too much heat generated from the application of cyanoacrylates onto human skin may cause discomfort in a patient to which they are applied. The exothermic effect of the compositions and a commercially available product was evaluated using an Infrared Thermometer to measure the temperature change on human skin. The skin temperature of patients was measured before and after the application of each composition type onto human skin. The average temperature increase after applying the compositions of the invention and the commercially available product were 0.25 and 0.41° C., respectively. The test results indicated that less heat is released from the application of the compositions than that of a commercially available product.

The compositions have a high flashpoint for safe use in the operating room or clinical surgery suite. A test was performed in accordance with ASTM D56-05, ISO 3679:2004 determination of flashpoint-rapid equilibrium closed cup method. The flashpoint for the microbial sealant compositions of the invention is greater than 240° F. The flashpoint of the 100% butyl cyanoacrylate microbial sealant compositions is about 227° F.

No cyanoacrylate residue was detected on a surgical blade through which an incision was made on a substrate covered with a microbial sealant drape compositions disclosed herein. The detection limit of the test was 5 ppm. The residue analysis on a surgical blade confirmed that no detectable cyanoacrylate sealants were transferred into the incision wound site.

The compositions provide a desirable degradation profile. The integrity (degradation over time) of a film produced from curing the compositions was evaluated following topical application to the skin of three pigs, and comparisons were made to commercially available drapes. The microbial sealant films applied at each application site were evaluated for degradation at approximately 8 hours after application, and 1, 2, 3, 4, 6, 8, 10, 12, 14, and 16 days after application. Degradation of both the disclosed microbial sealant film and the commercial product was evident by the first observation interval (8 hours after application). At this time, 2 out of 12 test sites with the disclosed microbial sealant film remained intact and 5 out of 12 sites with the predicate device were intact. When the study ended on day 16, the microbial sealant film of the invention was partially present in 2 of the 12 sites, while the commercial product was absent from all 12 sites.

The compositions are compatible with currently available skin preparation products, surgical incise drape products and wound closure products. Compatibility with current products includes application of the compositions without adversely affecting the performance of wound closure products and surgical incise drapes. Skin preparation products that may be used in concert with the compositions of the invention include without limitation ChloraPrep®, Duraprep™, 10% povidone iodine and Betadine®. Duraprep™ is preoperative skin preparation product comprising iodine povacrylex and isopropyl alcohol. ChloraPrep® is a rapid-acting, persistent, and broad-spectrum preoperative skin preparation product, which consists of 2% chlorhexidine gluconate in 70% isopropyl alcohol. Betadine® is a consumer-available topical antiseptics containing 10% of povidone-iodine. Surgical incise drapes may also be used with the cyanoacrylate compositions of the invention including without limitation 3M Steri-Strip™ and Loban™ 2. Steri-Strip™ is an antimicrobial skin closure product that is made of a porous, non-woven backing coated with a pressure-sensitive adhesive which contains iodophor and is reinforced with polyester filaments for improved strength. Loban™ 2 is an antimicrobial surgical incise drape with an iodophor impregnated adhesive providing a sterile surface and antimicrobial activity throughout the procedure. The compatibility of the compositions with other commercially available products used for preventing surgical site infections was investigated by observing the effect of the compositions on the adhesion property of surgical incise drape in the absence and presence of different skin preparation products.

The compositions are also compatible with currently available wound closure products. The wound closure products may include SurgiSeal®, Dermabond® and Steri-Strip™. Dermabond® is a liquid bonding adhesive that holds cuts, incisions and wounds together. SurgiSeal® is cyanoacrylate-based topical skin adhesive for the closure of wound and incisions to provide a flexible, water-resistant, antimicrobial protective coating, which provides the optimal balance between bond strength and flexibility.

The compositions are compatible with lasers. The lasers that may be used in concert with the compositions include without limitation $CO_2$, Nd:YAG, and Diode. The compositions are intended to be used after typical operative skin preparation prior to a surgical incision. Lasers may be required to be used for skin incision, ablation, or coagulation for a surgical procedure. The in vitro study was conducted to evaluate the effect of both free beam and contact use of the lasers on the disclosed microbial sealant film formed on pig skin. The combined use of a skin prep such as Betadine® with the compositions was also investigated using a diode laser. The integrity of the film produced by curing the compositions was evaluated by macroscopic observations for cracking, blistering and peeling. The intense thermal energy of the lasers was used to determine if the film would ignite. The results showed that the film did not ignite, crack, blister or peel for all three laser types when used with either free beam or contact thermal energy applications so that the sealant film maintains its integrity and effectiveness as a sealant for the surgical procedure. These same results were obtained when combined with the surgical skin preparation product when the diode laser was used with either free beam or contact laser.

The compositions are compatible with defibrillators and an electrocautery equipment. The in vitro study was conducted on porcine skin to evaluate the effect of the microbial sealant compositions on the performance of the defibrillator and electrocautery equipment. A microbial sealant composition was applied onto porcine skin. A metal plate or probe was attached on the underneath side of the porcine skin to measure the voltage of the defibrillator. In order to evaluate the compatibility with electrocautery techniques, a commercially available electrocautery device was used to make incisions and coagulations on the porcine skins covered with the disclosed microbial sealant film. The electrocautery settings were made at 70 watts for both incision and coagulation. The single coat application of the microbial sealant compositions did not significantly decrease the conductance of the energy being discharged from the defibrillator. There was no observation of ignition, blistering, cracking or peeling. When used with the electrocautery equipment, the microbial sealant compositions demonstrated desirable performance with regard to charring, plume discoloration and cleaning of the blade upon completion of the incision and coagulation.

The compositions provide a thin and uniform film on the surgical sites. In some preferred aspects the drape film has a thickness of from about 5 μm to about 400 μm when applied to the skin of a subject. More preferably, the drape film comprises a thickness of about 10 μm to about 200 μm, more preferably about 30 μm to about 80 μm, and more preferably about 50 μm to about 60 μm. The film thickness study indicates the formation of thin and uniform films of the compositions.

The compositions provide greater resistance to penetration of water by impact than other commercially available liquid drapes. The resistance of the microbial sealant compositions to the penetration of water by impact was investigated according to the American Association of Textile Chemists and Colorists (AATCC) test method. A volume of water is allowed to spray against the taut surface of the disclosed microbial sealant film backed by a weighted blotter. The blotter was then reweighed to determine water penetration. The compositions have an average value of 0.03 grams from penetration of water by impact compared to an average value of 0.07 grams for a commercial drape composition. The test results indicates that the compositions provide twice more resistance to water penetration by impact than the commercial product.

The compositions are safe and effective as a surgical sealant product useful for inhibiting surgical site infections, and as an adhesive product for securing an in-dwelling catheter in place. The safety and biocompatibility of the composition has been evaluated based on the International Organization for Standardization (ISO) 10993, Biological Evaluation of Medical Devices. Cytotoxicity was measured on the preferred liquid microbial sealant composition using an in vitro biocompatibility study. The liquid microbial sealant compositions are not cytotoxic. For comparison, the in vitro cytotoxicity of another device was also evaluated, which showed no evidence of causing cell lysis or toxicity. The compositions were also observed to be less irritating than the other device, which was confirmed by the primary skin irritation study and ISO intracutaneous study.

The liquid microbial sealant drape compositions are not genotoxic. Bacterial reverse mutation test, mouse peripheral blood micronucleus study and in vitro chromosomal aberration study in mammalian cells confirmed that the compositions are not genotoxic.

In order to reduce the bioburden, the cyanoacrylate-based microbial sealant drape compositions may be filtered through a 0.2 μm filter. The applicators with the overpack may also be sterilized with heat, ethylene oxide prior to the final E-beam or gamma irradiation.

The sterility of the cyanoacrylate-based microbial sealant drape compositions may be analyzed by bacteriostasis and fungistasis tests. In embodiments of the invention, a Sterility Assurance Level (SAL) should be obtained at a minimum of $10^{-3}$, which includes the probability of a single unit being non-sterile after sterilization is 1 in 1000. In more preferred embodiments, the Sterility Assurance Level may be at least $10^{-6}$.

The following examples are provided to describe the invention in greater detail. They are intended to illustrate, not to limit, the invention.

Example 1

Setting Time Measurement

Pig skin (4×4 square inch) was prepared by wiping the surfaces of the skin with sterile gauze saturated with isopropanol. All oily substances were thereby removed from the pig skin. The surface was wiped with sterile gauze to remove the isopropanol. The applicator containing the microbial sealant composition was opened and adhesive was permitted to saturate the sponge applicator tip for about 10 seconds prior to application. A thin film was applied to the pig skin after which elapsed time was recorded by a stop watch. Set time was then recorded by stopping the clock when the film was dry as determined at the point where no liquid transfer occurred when the film was touched with a gloved finger.

Example 2

Viscosity Measurement

The viscosity of the cyanoacrylate compositions were measured by the Brookfield DV-II+ viscometer. The spindle and cup were cleaned with acetone after each measurement. About 0.5 ml of the microbial sealant composition was put into the cup and the cup was brought into position and slowly secured with the retaining arm. The motor was turned on after the sample was equilibrated in the cup. The viscosity of the disclosed microbial sealant composition was measured in triplicate. Any residue was removed with acetone prior to next sample measurement.

Example 3

Average Set Time and Viscosity for Cyanoacrylate Mixtures

To a polyethylene bottle equipped with a magnetic stir bar, 24 g of n-butyl cyanoacrylate (BCA) was mixed with 56 g of 2-octyl cyanoacrylate (OCA) at room temperature for 4 hours (Composition 1). To a polyethylene bottle equipped with a magnetic stir bar, 32 g of n-butyl cyanoacrylate (BCA) was mixed with 48 g of 2-octyl cyanoacrylate (OCA) at room temperature for 4 hours (Composition 2). 3 lbs of n-butyl cyanoacrylate (BCA) was mixed with 12 lbs of 2-octyl cyanoacrylate (OCA) in a plastic container at room temperature for 4 hours. A trace amount of D & C Violet #2 was included in BCA and OCA as the colorant (Composition 3). Each of the three compositions was tested for average set time and average viscosity, as shown in Table 3.

TABLE 3

Average viscosity and set time of the preferred microbial sealant compositions.

| Composition | Avg. set time | Avg. viscosity |
|---|---|---|
| Composition 1 | 24.5 s | 3.68 cps |
| Composition 2 | 27.8 s | 3.88 cps |
| Composition 3 | 22.3 s | 3.88 cps |

Example 4

Effect of Microbial Sealant Composition on the Wound Closure Strength of Steri-Strip A skin model was used to evaluate the effect of the disclosed microbial sealant drape composition on the wound closure strength of commonly used wound closure products, 3M Steri Strips. Three (3) pig skin squares of skin model were randomly assigned to each of the following: a) no preparation product (untreated); b) liquid microbial sealant alone; c) Chloraprep alone; d) liquid microbial sealant drape applied over Chlorprep; e) Duroprep alone; f) liquid microbial sealant drape applied over Duroprep; g) Betadine alone; and h) liquid microbial sealant drape applied over Betadine. Following preparation of the incision site with skin preparation products and/or the disclosed liquid microbial sealant drape, an incision was made in the middle of the pig skin. The incisions were then closed with different wound closure products. After wound closure, the pig skin incisions were pulled apart using a Mark-10 tensiometer at a speed of 25 mm/min to determine wound closure strength. The data is summarized in Table 4.

TABLE 4

The Average Force Required for Separating Wound Closure of Steri-Strip on a Skin Model

| Sample Name | Sample 1 (lb-min/sq in) | Sample 2 (lb-min/sq in) | Sample 3 (lb-min/sq in) | Average Force (lb-min/sq in) |
|---|---|---|---|---|
| Untreated | 3.0 | 3.2 | 3.2 | 3.13 |
| Liquid microbial sealant | 9.4 | 7.6 | 8.8 | 8.60 |
| Betadine | 1.6 | 1.8 | 1.2 | 1.53 |
| Betadine and Liquid mcirobial sealant | 8.2 | 7.6 | 6.2 | 7.33 |
| Chloraprep | 3.0 | 3.0 | 3.2 | 3.07 |
| Chloraprep and Liquid microbial sealant | 10.6 | 7.8 | 7.0 | 8.47 |
| Duraprep | 2.4 | 3.0 | 2.2 | 2.53 |
| Duraprep and Liquid microbial sealant | 9.0 | 12.2 | 10.8 | 10.67 |

Example 5

Surface Coverage of the Disclosed Microbial Sealant Applicator

A liquid microbial sealant composition comprising 80% of 2-octyl cyanoacrylate and 20% of n-butyl cyanoacrylate was applied to pig skins from an applicator until all the adhesive (3.5 mL) was dispensed. The length and width of the covered areas was measured with electronic digital calipers. These values were used to calculate the surface coverage per applicator. The surface coverage was measured according to the following procedures. A 4×12 inch of pig skin was prepared by wiping the surfaces of the skin with sterile gauze saturated with isopropanol to make sure that all oily substances were removed from the pig skin. The surface of the skin was wiped dry with gauze. The microbial sealant composition was applied to the prepared pig skin until the entire adhesive in a single applicator was distributed (3.5 ml). The whole area of the pig skin was covered by diminishing the gap and overlap as much as possible and by keeping the strokes even. The width and length of pig skin covered with adhesive was measured using an electronic digital caliper. The surface area was calculated from the measured width and length. The average surface coverage of the drape composition disclosed in the invention device was approximately 222.0 inch$^2$.

Example 6

Film Thickness

The drape film thickness was measured using optical microscopy. The drape film compositions comprising 80% of 2-octyl cyanoacrylate and 20% of n-butyl cyanoacrylate were prepared by applying the drape composition from the applicator onto two adjacent glass slides. The cyanoacrylate compositions were allowed to dry. A razor blade was used to make a cut between the two glass slides to create a cross section in the cured film that was approximately in line with the glass slide edges. The glass slide with the cured drape film was mounted with a clamp on the metallographic microscope such that the cross section of the slide and the cured film could be viewed by optical microscopy. The specimen was magnified with the 20× lens. A series of measurements of film thickness were made by comparing the images of the samples with a standard optical image photographed at the same camera and microscope settings. Three measurements per sample were made per photograph and three photographs were taken per film for a total of 9 measurements per film. Under the test condition, the microbial sealant film has a thickness of less than about 500 µm.

Example 7

Cytotoxicity

Cytotoxicity was tested on a microbial drape composition comprising 80% of 2-octyl cyanoacrylate and 20% of n-butyl cyanoacrylate using an in vitro biocompatibility study based on ISO 10993, Part 5. The disclosed liquid drape composition was applied to both sides of a glass slide to cover an area 15 mm by 75 mm. The coated slides were allowed to dry prior to placing them into a container for extraction. The test article was extracted with a single strength Minimum Essential Medium (1×MEM) with 5% serum and 2% antibiotics. The test extract was placed onto three separate monolayers of L-929 mouse fibroblast cells propagated in 5% $CO_2$. High density polyethylene was used as the negative control and tin stabilized polyvinylchloride was used as the positive control. All monolayers were incubated at 37° C. in the presence of 5% $CO_2$ for 48 hours, which was then examined microscopically to determine any change in cell morphology. The liquid microbial sealant compositions of the invention did not cause cell lysis or toxicity.

Example 8

Genotoxicity Study I

A glass rod was cleaned with 70% isopropyl alcohol and allowed to air dry. The rod was then coated with a microbial sealant drape composition comprising 80% of 2-octyl cyanoacrylate and 20% of n-butyl cyanoacrylate up to 4 cm and allowed to dry for at least 1 minute prior to extraction with dimethyl sulfoxide (DMSO) and 0.9% sodium chloride at 37° C. for 72 hours. Another glass rod without cyanoacrylate liquid drape was similarly subjected to the extraction conditions for use as a negative control. Known mutagens, benzo [a]pyrene and 2-nitrofluorene, were used as positive control to demonstrate that tester strain TA 98 was sensitive to mutation reversion to wild type. For tester strains TA100 and TA 1535, sodium azide and 2-aminoanthracene were used as positive controls. For tester 1537, 2-aminoanthracene and ICR-191 were used as positive controls. For tester strain WP2uvrA, 2-aminoanthracene and methylmethane-sulfonate were used as positive controls.

Tubes containing molten top agar supplemented with tryptophan for the *Escherichia coli* or with histidine-biotin solution for the *Salmonella typhimurium* were inoculated with culture for each of the five tester strains and with the DMSO and saline extracts of the disclosed cyanoacrylate liquid drape film. Sterile water for injection (SWI) or S9 homogenate simulating metabolic activation was added as necessary. Trytophan-free media plates (for *E. coli*) and histidine-free media plates (for *S. typhimurium*) were prepared in triplicate as follows: 1) DMSO and saline extracts of the cyanoacrylate liquid drape film with and without S9 activation; 2) negative controls with and without S9 activation; and 3) positive controls with different tester strains in the absence and presence of S9 activation.

The plates were incubated at 37° C. for 2 to 3 days. Following the incubation period, the revertant colonies on each plate were recorded. The mean number of revertants and standard deviation was determined. The mean number of revertants of the test plates was compared to the mean number of revertants of the negative control for each of the five tester strains. It was concluded that, under the study conditions, the disclosed liquid microbial sealant compositions in both DMSO and saline extracts were not mutagenic to *Salmonella Typhimurium* strains (TA98, TA100, TA1535, and TA1537), and were not mutagenic to tryptophan-dependent *Escherichia coli* strain WP2uvrA.

Example 9

Genotoxicity Study II

A glass rod was cleaned with 70% isopropyl alcohol and allowed to air dry, and then coated with the microbial sealant drape compositions comprising 80% of 2-octyl cyanoacrylate and 20% of n-butyl cyanoacrylate up to 4 cm. The drape was allowed to dry for at least 1 minute prior to extraction with dimethyl sulfoxide (DMSO) and 0.9% sodium chloride at 37° C. for 72 hours. Additional test rods without cyanoacrylate microbial sealant were subjected to the same extraction conditions as the test article and were used as negative controls. Methyl methanesulfonate (MMS) in saline, an antineoplastic drug known to have mutagenic properties, was used as a positive control.

Five groups of mice, each of which consisted of 6 male and 6 female, were injected with cyanoacrylate liquid drape in SC extract, cyanoacrylate liquid drape in SO extract, negative control in SC, negative control in SO, and positive control with methyl methanesulfonate, respectively. Each mouse received an intraperitoneal injection at a dose of 20 ml/kg of the appropriate extract accordingly for consecutive three days. All animals were observed immediately following injection and on a daily basis to access general health. On day 4, blood was collected from the tail veins of each mouse and solutions were prepared. The normochromatic erythrocytes were evaluated for the presence of micronuclei. The frequency of micronucleated reticulocytes (MN-RETs) was determined and used as an index of genotoxicity. The frequency of reticulocytes relative to total erythrocytes was calculated as an indication of stem cell toxicity. Both SC and SO extracts of the cyanoacrylate liquid drapes of the invention did not show statistically significant increases in the frequency of MN-RETs. Cyanoacrylate liquid microbial sealant compositions of the invention are not genotoxic under the study conditions. Also, there was no evidence of cellular toxicity from extracts of the disclosed cyanoacrylate liquid drape composition.

Example 10

Local Irritation and Toxicity Study

Local irritation or toxicity effect after implantation of the microbial sealant drape compositions comprising 80% of 2-octyl cyanoacrylate and 20% of n-butyl cyanoacrylate was conducted to evaluate the potential for a local irritant or toxic response to the drape implanted in direct contact with muscle tissue. High density polyethylene was used as the negative control. Three Albino New Zealand rabbits were used for the test. One incision was made on each side of the rabbit back. The fascia was cut to expose the paravertebral muscle. A pocket was formed with a hemostat between the muscle fibers into which the implant material was introduced. After four weeks, the rabbits were weighed and then euthanized by an intravenous injection of a sodium pentobarbital based drug. The paravertebral muscles were dissected free and fixed in 10% neutral buffered formalin to facilitate cutting. The tissue was macroscopically examined using low magnification to look for capsule formation or other signs of irritation. The excised sections were also histologically processed for microscopic evaluations. The disclosed microbial sealant drapes of the invention caused no macroscopic reaction under the study conditions, while microscopic examination indicated the disclosed composition was moderately irritating to the tissue.

Example 11

ISO Intracutaneous Study

Intracutaneous study of microbial sealant drape compositions comprising 80% of 2-octyl cyanoacrylate and 20% of n-butyl cyanoacrylate was conducted to determine whether leachables extracted from the disclosed microbial sealant composition wound cause local dermal irritant effects following injection into rabbit skin. The glass rods were wiped clean with 70% isopropyl alcohol and allowed to air dry. The glass rod was coated with the disclosed microbial sealant compositions up to 4 cm and allowed to air dry for at least one minute prior to placing in the extraction container. The test article was extracted in 0.9% sodium chloride USP solution (SC) and sesame oil, NF 9 (SO) at 37° C. for 72 hours. A 0.2 ml dose of the test article extract was injected by the intracutaneous route into five separate sites on the right side of the back of each rabbit. Injections were spaced approximately 2 cm apart. The appearance of each injection site was noted immediately after injection. Observations for erythema and edema were conducted at 24, 48, and 72 hours after injection. Under the conditions of this study, there was no erythema and no edema from the SC extract injected intracutaneously into rabbits. There was very slight erythema and very slight edema from the SO extracts injected intracutaneously into rabbits.

Example 12

ISO Skin Irritation Study

Skin irritation study of cyanoacrylate-based microbial sealant drape compositions comprising 80% of 2-octyl cyanoacrylate and 20% of n-butyl cyanoacrylate was conducted to evaluate the potential for a single topical application of the disclosed microbial sealant composition to irritate skin. New Zealand white male rabbits were used for this study. On the day of treatment, four sites, two on each side of the back cranially and caudally, were designated on each rabbit. A 0.5 ml portion of the disclosed microbial sealant composition was applied topically to each cranial site by introduction under a 4 ply gauze layer to an area of skin approximately 25 mm×25 mm square. The patches were backed with plastic and covered with a nonreactive tape. After the 24 hour exposure, the binders, tape and patches were removed. The sites were graded for erythema and edema at 1, 24, 48 and 72 hours after removal of the single sample application. Under the conditions of the study, very slight erythema and no edema were observed on the skin of the rabbits. The primary irritation index for the microbial sealant composition was calculated to be 0.7.

Example 13

Residue Analysis

The residue analysis on surgical blade was determined on a pig skin model. A microbial sealant drape composition comprising 20% butyl cyanoacrylate and 80% octyl cyanoacrylate was applied to pig skin as the sealant before incision. An incision was made through the drape film using a surgical blade. The surgical blade was then immersed in HPLC grade acetone to extract any possible cyanoacrylate residue. The acetone solution after extraction was analyzed by GC/MS to determine if any residual cyanoacrylate was left on the blade after an incision was made. The fresh surgical blade cutting through pig skin without treatment by microbial sealants served as a negative control. Solution of polymer film of the preferred microbial sealant composition in acetone was used as the positive control to determine the detection limit of GC/MS.

In order to determine the limit of detection, positive controls were run and various peaks were compared to determine which peaks were best for assessing the presence of the materials. A peak associated with cyanoacrylate at 14.7 minutes was found to be best for quantification and detection of cyanoacrylate. At 5 ppm, the peak at 14.7 minutes for cyanoacrylate was observed clearly with a large ratio of signal/noise, which was thus assigned as the detection limit. Following the same condition used for the positive control, the residual analysis of surgical blade used to cut through the drape film of the preferred compositions in the invention was conducted. No cyanoacrylate was detected indicating that no residue of the disclosed drape composition on surgical blade was found at the detection limit of 5 ppm. There was no cracking, blistering or flaking of the drape film observed when the incision was made on the microbial sealant of the preferred composition disclosed herein. These observations suggest that the microbial sealant compositions provide the desirable flexibility and strong bonding strength.

Example 14

Adhesion Properties

A pig skin model was used to evaluate the effect of the microbial sealant drape compositions on the adhesion property of the commonly used surgical incise drapes with and without the treatment of the skin preparation products. The following treatments were subjected to the pig skin model test: a) no preparation product (untreated); b) liquid microbial sealant alone; c) ChloraPrep® alone; d) liquid microbial sealant applied over ChloraPrep®; e) DuraPrep™ alone; f) liquid microbial sealant applied over DuraPrep™; g) 10% povidone iodine alone; and h) liquid microbial sealant applied over 10% povidone iodine. The skin model was prepared by applying different skin preparation products and the liquid microbial sealant, after which a surgical incise drape such as 3M Steri-Strip® and Loban™ 2 was applied to the surface of each model. The surgical incise drape was then peeled away from the skin model using a Mark-10 tensiometer to determine the adhesion strength of the incise drape at a speed of 50 mm/min.

Table 5 shows the average force required to peel Steri-Strip® from the pig skin treated under various conditions. Compared to skin models untreated or treated only with skin preparation products, the adhesion strengths of Steri-Strip® on skin models with the liquid microbial sealants of the invention are 2-3 times greater. The test results demonstrate that the use of the composition improves the adhesion strength of the commonly used surgical incise drapes. The surgical incise drape provides increased adhesion strength when applied to the substrates sequentially treated with the skin preparation products and the liquid microbial sealants compared to those applied to the substrates treated only with the skin preparation products. These observations indicate that the liquid microbial sealant is compatible with commercial surgical incise drapes and skin preparation products and provides increased adhesion strength.

TABLE 5

Average strength required to peel Steri-Strip ® from the pig skin model

| Treatment | Average strength (lb/in$^2$) |
|---|---|
| Untreated | 0.67 |
| Liquid microbial sealant | 1.40 |
| A commercial liquid drape | 1.20 |
| Povidone iodine | 0.67 |
| Povidone iodine + liquid microbial sealant | 1.67 |
| Povidone iodine + a commercial liquid drape | 1.40 |
| ChloraPrep ® | 0.67 |
| ChloraPrep ® + liquid microbial sealant | 1.20 |
| ChloraPrep ® + a commercial liquid drape | 1.20 |
| DuraPrep ™ | 0.53 |
| DuraPrep ™ + liquid microbial sealant | 1.67 |
| DuraPrep ™ + a commercial liquid drape | 1.33 |

Example 15

Compatibility with Wound Closure

A pig skin model was used to evaluate the effect of the disclosed microbial sealant drape composition on the wound closure strength of the wound closure products with and without pre-treatment with skin preparation products. The testing skin models were randomly assigned to the following treatments: a) no preparation product (untreated); b) liquid cyanoacrylate microbial sealant alone; c) ChloraPrep® alone; d) liquid microbial sealant applied over ChloraPrep®; e) DuraPrep™ alone; f) liquid cyanoacrylate microbial sealant applied over DuraPrep™; g) Betadine® alone; and h) liquid cyanoacrylate microbial sealant applied over Betadine®. Following preparation of the incision site with skin preparation products and/or the liquid microbial sealant, an incision was made in the middle of the pig skin. The incisions were then closed with different wound closure products. After wound closure, the pig skin incisions were pulled apart after 1-2 minutes using a Mark-10 tensiometer at a speed of 25 mm/min to determine the wound closure strength.

The average wound closure strength of SurgiSeal® in the absence and presence of different skin preparation products and/or the liquid microbial sealant drape compositions is summarized in Table 4. The compositions and different skin preparation products including Betadine®, ChloraPrep® and DuraPrep™, were evaluated for the effect on the wound strength of SurgiSeal®. As shown in Table 6, the wound closure strength of SurgiSeal® in the presence of the liquid microbial sealant is slightly greater than that in the absence of the liquid microbial sealant. Likewise, the wound closure strength of other wound closure products such as Dermabond® and Steri-Strip® is stronger when liquid microbial sealant drapes are applied as compared to that without applying the liquid cyanoacrylate microbial sealant. These observations indicate that the liquid cyanoacrylate microbial sealant is compatible with commercially available wound closure products and provides for improved closure strength.

TABLE 6

The Average Force Required for disrupting Wound Closure of SurgiSeal ® on a Skin Incision Model

| Treatment | Average strength (lb) |
| --- | --- |
| Untreated | 4.5 |
| Liquid microbial sealant | 8.9 |
| Betadine ® | 4.7 |
| Betadine ® + liquid microbial sealant | 6.9 |
| ChloraPrep ® | 4.7 |
| ChloraPrep ® + liquid microbial sealant | 5.9 |
| DuraPrep ™ | 4.8 |
| DuraPrep ™ + liquid microbial sealant | 6.1 |

Example 16

Skin Irritation

Skin irritation study of a cyanoacrylate-based liquid microbial sealant drape compositions comprising 80% of 2-octyl cyanoacrylate and 20% of n-butyl cyanoacrylate was conducted to evaluate the potential for a single topical application of the microbial sealant composition to irritate skin. New Zealand white male rabbits were used for this study. Under the conditions of this study, very slight erythema and no edema were observed on the skin of the rabbits for the disclosed microbial sealant composition. The primary irritation index for the microbial sealant composition was calculated to be 0.7, while the primary irritation index for the predicate device was calculated to be 1.4.

Example 17

Intracutaneous Study

Intracutaneous study of microbial sealant drape compositions comprising 80% of 2-octyl cyanoacrylate and 20% of n-butyl cyanoacrylate was conducted to determine whether leachables extracted from the composition wound cause local dermal irritant effects following injection into rabbit skin. For comparison, the corresponding study was also conducted for a commercial liquid drape. The test article was extracted in 0.9% sodium chloride USP solution (SC) and sesame oil, NF 9 (SO). A 0.2 ml dose of the test article was injected by the intracutaneous route into five separate sites on the right side of the back of each rabbit. Observations for erythema and edema were conducted at 24, 48, and 72 hours after injection. As shown in Table 7, there was no erythema and no edema from the SC extract of the disclosed microbial sealant composition injected intracutaneously into rabbits. There was very slight erythema and very slight edema from the SO extract of the microbial sealant composition injected intracutaneously into rabbits with a mean difference score of 0.3. In comparison, there was well-defined to moderate erythema and well-defined to severe edema from the SO extract of a commercial liquid drape, injected intracutaneously into rabbits with a mean difference score of 2.1.

TABLE 7

Summary of ISO intracutaneous study

| Test article | Extract | Test group mean score | Control group mean score | Mean difference score (test – control) |
| --- | --- | --- | --- | --- |
| 20% BCA and 80% OCA | SC | 0.0 | 0.0 | 0.0 |
|  | SO | 0.8 | 0.5 | 0.3 |
| A commercial liquid drape | SO | 2.6 | 0.5 | 2.1 |

| SCORE | ERYTHEMA | EDEMA |
| --- | --- | --- |
| 0 | No erythema | No edema |
| 1 | Very slight erythema (barely perceptible) | Very slight edema (barely perceptible) |
| 2 | Well-defined erythema | Well-defined edema (edges of area well-defined by definite raising) |
| 3 | Moderate erythema | Moderate edema (raised approximately 1 mm) |
| 4 | Severe erythema (beet redness) to eschar formation preventing grading of erythema | Severe edema (raised more than 1 mm, and extending beyond exposure area) |

Example 18

In Vitro Bacteria Immobilization

Sterile pig skin, 4×4 inches, was aseptically cut into 4×1 cm pieces. Each piece of the sterile pig skin was inoculated with 0.1 mL (about 75,000 colony forming units) of MRSA, *S. epidermids, Pseudomonas aeruginosa, Candida albicans*, or *Corynebacterium* sp. to a marked 4×1 cm area of the skin. The incision site was defined by a metric ruler to the depth of the fat layer below the dermis and length of about 4 cm. The inoculated skin was placed under a laminar flow hood to allow the inoculum to dry at ambient laboratory temperature. A microbial sealant composition comprising 20% butyl cyanoacrylate and 80% octyl cyanoacrylate was then applied onto the inoculated skin over the incision site. An incision was then made with a sterile scalpel and the pig skin was manipulated by gently squeezing the incision site to simulate surgical trauma. Excess skin was cut away from the incision site with a sterile scalpel. To determine whether organism had migrated from the skin surface to the incision site, the incision site was irrigated with 0.1 mL of sterile elution fluid and the eluate was collected. Ten-fold serial dilutions of the eluate were prepared and duplicate pour plate counts and membrane filtration count were performed. The agar plates were incubated for 48 to 72 hours at 35-37° C. Analysis of data shows that the microbial sealant compositions were at least >99% effective in preventing the spread of the microorganisms into the wound site.

Example 19

In Vivo Bacteria Immobilization

A total of 60 healthy volunteers (29 females and 31 males) were recruited to evaluate the in vivo bacteria immobilization of a microbial sealant composition comprising 20% butyl cyanoacrylate and 80% octyl cyanoacrylate. The study included a 14-day pretreatment washout period for stabilization of skin bacteria flora. During the washout period, subjects refrained from using any topical antimicrobials, systemic antibiotics, medical soaps, lotions, shampoos, etc, for at least two weeks before the evaluation and throughout the study. The tested area consisted of the right inguinal region. Hair was removed using a sterile disposable dipper device. A sterile drape was used to isolate the inguinal area from the rest of the body and then a surgical marker was used to draw four different 1 inch squares separated by 1 inch of normal skin in which the microbial sealant composition was applied. Using sterile gloves the products were applied onto the skin in its designated areas and allowed to dry. Sterile gauze was placed over the test area to avoid subsequent contamination. Swabbed samples from skin were collected at 15 minutes, 4 hours and 24 hours after the initial application of the microbial sealant composition. The sample collection procedure was performed using a sterile technique including sterile gloves, sterile microbial sealants, surgical masks and hats. After the sampling was completed the entire contents of the tube was poured carefully onto a 1 mL Petrifilm™ aerobic plate (plate count agar) and the plates were incubated for 48 hours at 30° C. A Petrifilm™ plate was used to quantify colony counts. At 15 minutes, the absolute log reduction was 5.568 for the disclosed microbial sealant composition. The absolute log reduction of bacteria for the microbial sealant composition is 4.299 and 3.33 at 4 hours and 24 hours, respectively.

Example 20

In Vitro Chromosomal Aberration Study in Mammalian Cells

A chromosomal aberration study was conducted to determine whether an extract of the microbial sealant drape composition wound cause clastogenic changes in Chinese Hamster Ovary (CHO). A glass rod was sterilized with 70% isopropyl alcohol and allowed to air dry. The glass rod was then coated (4 cm) with a microbial sealant composition comprising 20% butyl cyanoacrylate and 80% octyl cyanoacrylate and allowed to air dry for at least 1 minute prior to placing the coated rod in the extraction container. A single preparation was extracted with DMSO with agitation at 37° C. for 72 hours. Following extraction, the DMSO extract was diluted with McCoy's 5A medium to a final concentration of 25% prior to testing. Aveclor 1254=induced rat liver (S9 homogenate) was used as metabolic activation. The S9 homogenate is prepared from male, Sprague Dawley rats. An uncoated glass rod was subjected to the same extraction conditions to serve as a negative control. A known direct acting genotoxic compound, Mitomycin C (MMC), was used as a positive control to demonstrate that CHO cells were sensitive to mutagens in the absence of metabolic activation. The microbial sealant composition extract, negative control, and positive control were tested in triplicate.

For the assays conducted without metabolic activation, the growth medium in each of three test culture flasks was replaced with 10 ml of the prepared extracts. For the assay conducted with metabolic activation, the test samples were supplemented with isocitrate dehydrogenase (NADP+) at 60 µl/ml and S9 at 20 µl/ml. After 18 hours of incubation at 37° C. in the presence of $CO_2$, the medium was decanted and the cultures were rinsed twice with 4-6 ml of calcium magnesium free phosphate buffered saline (CMF-PBS). The flasks were incubated for an additional 2 hours at 37° C. After harvesting, slides of the cells were prepared, stained with Giemsa, and examined microscopically for chromosomal aberrations at 100× magnification. Under the conditions of this assay, the DMSO test extract of the disclosed microbial sealant composition was not considered genotoxic to Chinese Hamster Ovary cells in the absence of S9 metabolic activation. The prepared McCoy's extract was not considered genotoxic to Chinese Hamster Ovary cells in the presence or absence of S9 metabolic activation. The positive and negative controls performed as expected.

Example 21

Resistance to Impact Penetration

The resistance of a microbial sealant drape composition comprising 20% butyl cyanoacrylate and 80% octyl cyanoacrylate to the penetration of water by impact was evaluated by following the American Association of Textile Chemists and Colorists (AATCC) test method. Test sample films of the microbial sealant composition were made that measured 178×230 mm. The samples and the blotting paper were conditioned in an atmosphere of 65±2% relative humidity (RH) at 21±1° C. for 4 hours before testing. After clamping the film onto an inclined stand, a standard blotter 152×230 mm was weighed and inserted beneath the test sample. A 500±10 ml volume of distilled water at 27±1° C. was poured into a funnel of the tester and allowed to spray onto the test sample of the microbial sealant composition. After the spraying, the test sample was carefully lifted, the blotter removed and reweighed to determine the amount of water that penetrated the film during the test. The mean value for the microbial sealant composition was 0.03 grams. Under the same conditions a commercial microbial sealant film comprised of 100% butyl cyanoacrylate displayed a mean value of 0.07 grams.

Example 22

Sealant Film Integrity Over Time

The integrity (degradation over time) of a microbial sealant composition comprising 20% butyl cyanoacrylate and 80% octyl cyanoacrylate was evaluated following topical application to the skin of three pigs and compared to another microbial sealant product. The pigs were restrained in a sling for up to 30 minutes during the application procedures. To reduce possible stress at being restrained in the sling, the pigs were initially conditioned to the sling over the course of 3 days prior to commencement of the application procedures. The day prior to treatment, each pig was weighed and placed in a sling. The hair on the dorso-lateral area was removed. The depilated skin was washed with povidone iodine scrub, rinsed well with water, and dried. On the day of the application procedure, each pig was placed in a sling. The depilated area of the back was scrubbed with povidone iodine, wiped with 70% isopropyl alcohol and painted with 10% povidone iodine antiseptic. The microbial sealant composition of the invention and another commercial drape were applied to four sites approximately 1×2 inches in area. The applied drape film at each application site was evaluated for degradation at approximately 8 hours after application, and 1, 2, 3, 4, 6, 8, 10, 12, 14, and 16 days after application. Degradation of both microbial sealant films was evident by the first observation interval (8 hours after application). At this time, 2 out of 12 test sites with the microbial sealant film of the invention remained intact and 5 out of 12 sites with the commercial film were intact. When the study ended on day 16, the microbial sealant film of the invention was partially present in only 2 of the 12 sites, while the commercial film was absent from all 12 sites.

Example 23

Gamma Radiation-Sterilization of Cyanoacrylate Compositions

Compositions comprising stabilized mixtures of about 80% 2-OCA and about 20% n-BCA were sterilized by gamma irradiation, and subject to advanced aging analysis to evaluate the effects of shelf storage on the sterilized composition, in terms of viscosity changes and set time of the composition. In the experiments described below, advanced aging was carried out using the ASTM F1980-07 standard.

Three batches of the composition stabilized with butylated hydroxyl anisole and sulfur dioxide were prepared (Samples 1, 2, and 3), and the viscosity of samples of each composition was measured before sterilization and after receiving different doses of gamma irradiation. Experiments were carried out in triplicate, and the results are shown in Table 8. The results showed that the initial viscosity of the composition was low, ranging from about 5.55 to about 5.98 cps, and that this viscosity did not increase substantially after the composition was dosed with gamma irradiation, with the post-irradiation viscosity ranging from about 6.03 to about 7.28 cps, or about 1.5% to about 30% on average.

TABLE 8

Viscosity before and after gamma irradiation at different doses.

| | | Viscosity (cps) | | | | | | | |
| | | Before Sterilization | | | | After Sterilization | | | |
| Sample | Gamma Dose (kGy) | 1 | 2 | 3 | Avg. | 1 | 2 | 3 | Avg. |
|---|---|---|---|---|---|---|---|---|---|
| 1 | 12.5-14.0 | 5.98 | 5.95 | 5.95 | 5.96 | 6.06 | 6.06 | 6.03 | 6.05 |
| 1 | 15.9-17.4 | 5.98 | 5.95 | 5.95 | 5.96 | 7.11 | 7.17 | 7.2 | 7.16 |
| 1 | 16.6-17.7 | 5.98 | 5.95 | 5.95 | 5.96 | 6.75 | 6.72 | 6.75 | 6.74 |
| 2 | 12.2-13.9 | 5.58 | 5.55 | 5.61 | 5.58 | 7.28 | 7.25 | 7.23 | 7.25 |

Sample 2 compositions were sterilized by gamma irradiation (12.2 to 13.9 kGy), and subject to an advanced aging study (F1980-07) for thirteen days. On days 3, 7, 10, and 13, samples were taken and the viscosity of each sample was measured; viscosity was also measured prior to the advanced aging study (day 0). Samples were also evaluated for their set time using a standard pig skin assay. The results are shown in Table 9. Advanced aging did not substantially affect set time.

TABLE 9

Viscosity and set time.

| Days in Advanced Aging at 80 degrees C. | Average Viscosity (cps) | Average Set Time (sec) on Pig Skin. |
|---|---|---|
| 0 | 6.76 | 30 |
| 3 | 8.04 | 30 |
| 7 | 13.5 | 30 |

TABLE 9-continued

Viscosity and set time.

| Days in Advanced Aging at 80 degrees C. | Average Viscosity (cps) | Average Set Time (sec) on Pig Skin. |
|---|---|---|
| 10 | 23.7 | 30 |
| 13 | 66.4 | 40 |

Example 24

Real Time Aging of Electron Beam Radiation-Sterilized Cyanoacrylate Compositions Compositions comprising stabilized mixtures of about 80% 2-OCA and about 20% n-BCA were sterilized by electron beam (E-beam) irradiation, and subject to real time aging analysis to evaluate the effects of shelf storage on the sterilized composition, in terms of viscosity changes and set time of the composition.

Three batches of the composition stabilized with butylated hydroxyl anisole and sulfur dioxide were prepared (Samples A, B, and C), and the viscosity of each composition was measured before sterilization and after receiving E-beam irradiation. Experiments were carried out in triplicate, and the results are shown in Table 10. The results showed that the initial viscosity of the composition was low, ranging from about 5.55 to about 6.03 cps, and that this viscosity did not increase substantially after the composition was dosed with irradiation, with the post-irradiation viscosity ranging from about 6.13 to about 7.97 cps, or about 10% to about 28% on average.

TABLE 10

Viscosity before and after E-beam irradiation.

| | Viscosity (cps) | | | | | | | |
| | Before Sterilization | | | | After Sterilization | | | |
| Sample | 1 | 2 | 3 | Avg. | 1 | 2 | 3 | Avg. |
|---|---|---|---|---|---|---|---|---|
| A | 5.97 | 5.91 | 5.79 | 5.89 | 7.36 | 7.36 | 7.97 | 7.56 |
| B | 6.03 | 5.94 | 5.84 | 5.94 | 6.74 | 6.74 | 6.13 | 6.54 |
| C | 5.58 | 5.55 | 5.61 | 5.58 | 6.74 | 7.36 | 6.74 | 6.95 |

Compositions were sterilized by E-beam irradiation, and subject to real-time aging studies for 24 months. Samples were taken at months 6, 9, 12, 15, and 24 and the viscosity of each sample was measured; viscosity was also measured prior to the study (Month 0). Samples were also evaluated for their set time using a standard pig skin assay. The results are shown in Table 11 and Table 12. Real time aging did not substantially affect set time.

TABLE 11

Real time shelf life stability for E-beam sterilized cyanoacrylate monomer adhesives (First).

| Month in Real Time | Viscosity test 1 (cps) | Viscosity test 2 (cps) | Viscosity test 3 (cps) | Avg. viscosity (cps) | Set Time test 1 (sec) | Set Time test 2 (sec) | Set Time test 3 (sec) | Set Time test 4 (sec) | Avg. Set Time (sec) |
|---|---|---|---|---|---|---|---|---|---|
| 0 | 5.97 | 5.91 | 5.79 | 5.89 | 24 | 25 | 25 | no data | 24.7 |
| 6 | 6.74 | 7.97 | 6.13 | 6.95 | 23 | 23 | 17 | no data | 21.0 |
| 9 | 6.74 | 6.74 | 7.97 | 7.15 | 25 | 25 | 25 | 25 | 25.0 |
| 12 | 9.19 | 9.81 | 9.81 | 9.60 | 20 | 20 | 20 | 20 | 20.0 |
| 15 | 12.3 | 11.6 | 11.6 | 11.8 | 25 | 25 | 25 | 25 | 25.0 |
| 24 | 14.6 | 14.5 | 14.4 | 14.5 | 20 | 20 | 20 | 20 | 20.0 |

TABLE 12

Real time shelf life stability for E-beam sterilized cyanoacrylate monomer adhesives (Second Test).

| Month in Real Time | Viscosity test 1 (cps) | Viscosity test 2 (cps) | Viscosity test 3 (cps) | Avg. viscosity (cps) | Set Time test 1 (sec) | Set Time test 2 (sec) | Set Time test 3 (sec) | Set Time test 4 (sec) | Avg. Set Time (sec) |
|---|---|---|---|---|---|---|---|---|---|
| 0 | 4.29 | 4.90 | 5.52 | 4.90 | 25 | 28 | 30 | 27 | 27.5 |
| 6 | 5.52 | 6.13 | 6.13 | 5.92 | 28 | 30 | 30 | 32 | 30.0 |
| 9 | 5.52 | 5.52 | 5.52 | 5.52 | 30 | 28 | 34 | 30 | 30.5 |
| 12 | 6.13 | 5.52 | 6.13 | 5.92 | 36 | 34 | 32 | 32 | 33.5 |
| 15 | 9.81 | 9.81 | 9.81 | 9.81 | 42 | 40 | 42 | No data | 41.3 |
| 24 | 13.5 | 14.1 | 12.9 | 13.5 | 59 | 58 | 63 | No data | 60.0 |

In a separate experiment, unsterilized compositions were subject to an advanced aging study at 80 degrees C. for 13 days (ASTM F1980-07). Samples were taken after sterilization but before advanced aging, and after 13 days of advanced aging, and the viscosity of each sample was measured. The results are shown in Table 13.

TABLE 13

Viscosity before and after advanced aging at 80 degrees C.

| | Viscosity (cps) | | | | | | | |
|---|---|---|---|---|---|---|---|---|
| | Post-sterilization, before advanced aging | | | | Post-sterilization, post-advanced aging | | | |
| Lot | 1 | 2 | 3 | Avg. | 1 | 2 | 3 | Avg. |
| 1 | 3.04 | 4.90 | 4.29 | 4.08 | 4.90 | 4.90 | 4.90 | 4.90 |
| 2 | 3.22 | 3.12 | 3.17 | 3.17 | 7.84 | 7.61 | 7.64 | 7.69 |
| 3 | 5.34 | 5.31 | 5.31 | 5.32 | 15.2 | 15.2 | 15.4 | 15.3 |
| 4 | 5.58 | 5.55 | 5.61 | 5.58 | 9.24 | 9.09 | 9.00 | 9.11 |
| 5 | 5.61 | 5.61 | 5.61 | 5.61 | 7.26 | 7.20 | 7.20 | 7.22 |
| 6 | 6.03 | 5.94 | 5.84 | 5.94 | 7.68 | 7.56 | 7.56 | 7.60 |
| 7 | 5.97 | 5.91 | 5.79 | 5.89 | 7.35 | 7.38 | 7.38 | 7.37 |
| 8 | 5.64 | 5.55 | 5.49 | 5.56 | 7.89 | 7.59 | 7.59 | 7.69 |
| 9 | 6.18 | 6.09 | 6.06 | 6.11 | 8.64 | 8.46 | 8.31 | 8.47 |

Example 25

Real Time Aging of Gamma Radiation-Sterilized Cyanoacrylate Compositions

Compositions comprising stabilized mixtures of about 80% 2-OCA and about 20% n-BCA were sterilized by gamma irradiation, and subject to real time aging analysis to evaluate the effects of shelf storage on the sterilized composition, in terms of viscosity changes and set time of the composition. The compositions were sterilized with gamma radiation at a dose of 12.2-13.9 kGy.

A single batch of the composition stabilized with butylated hydroxyl anisole and sulfur dioxide was prepared, and the viscosity of the composition was measured before sterilization and after receiving gamma irradiation. The composition was subject to a real time aging study that had progressed to 15 months at the time of this disclosure, and will continue up to 18 months. Experiments were carried out in triplicate, and the results are shown in Table 14. Table 14 shows the results of the real time aging as of month 15 post-gamma sterilization. The results showed that the initial viscosity of the composition was low, ranging from about 3.12 to about 3.22 cps. Samples were taken at months 5, 6, 7, 8, 9, 11, 12, and 15, and the viscosity of each sample was measured.

TABLE 14

Viscosity before and after gamma irradiation.

| Month in real time | Viscosity test 1 (cps) | Viscosity test 2 (cps) | Viscosity test 3 (cps) | Avg. viscosity (cps) |
|---|---|---|---|---|
| Initial | 3.22 | 3.12 | 3.17 | 3.17 |
| 5 | 6.79 | 6.74 | 6.74 | 6.76 |
| 6 | 7.56 | 7.53 | 7.53 | 7.54 |
| 7 | 8.66 | 8.63 | 8.66 | 8.65 |
| 8 | 8.48 | 8.48 | 8.40 | 8.45 |
| 9 | 7.33 | 7.33 | 7.36 | 7.34 |
| 11 | 12.5 | 12.4 | 12.4 | 12.4 |
| 12 | 12.4 | 12.3 | 12.3 | 12.3 |
| 15 | 19.8 | 19.7 | 19.7 | 19.7 |

Samples were also evaluated for their set time using a standard pig skin assay. The results are shown in Table 15. Real time aging did not substantially affect set time.

TABLE 15

Composition set time after gamma irradiation.

| Month in real time | Set Time Test 1 (sec) | Set Time Test 2 (sec) | Set Time Test 3 (sec) | Set Time Test 4 (sec) | Avg. Set Tim (sec) |
|---|---|---|---|---|---|
| Initial | 25 | 25 | 25 | 25 | 26.3 |
| 5 | 30 | 30 | 30 | 30 | 30 |
| 6 | 30 | 30 | 30 | 30 | 30 |
| 7 | 30 | 30 | 30 | 30 | 30 |
| 8 | 30 | 30 | 30 | 30 | 30 |
| 9 | 30 | 30 | 30 | 30 | 30 |
| 11 | 30 | 35 | 30 | 35 | 32.5 |
| 12 | 30 | 30 | 35 | 35 | 32.5 |
| 15 | 35 | 35 | 35 | 35 | 35 |

The invention is not limited to the embodiments described and exemplified above, but is capable of variation and modification within the scope of the appended claims.

We claim:

1. A method for inhibiting bacterial infection of the skin, comprising applying a cyanoacrylate adhesive composition to the skin and allowing the composition to cure on the skin, thereby reducing bacteria colonization on the skin, wherein the composition comprises a mixture of about 78% to about 82% by weight of monomeric 2-octyl cyanoacrylate, about 22% to about 18% by weight of monomeric n-butyl cyanoacrylate, about 2000 ppm to about 14,000 ppm of butylated hydroxyl anisole, and about 10 ppm to about 200 ppm of sulfur dioxide or about 5 ppm to about 50 ppm of an acid stabilizer selected from the group consisting of sulfuric acid, phosphoric acid, and perchloric acid, wherein the composition is sterilized by electron beam (E-beam) irradiation, wherein the viscosity of the sterilized composition increases by no more than about 300% over a period of at least two years of shelf storage, and wherein the composition does not contain any plasticizer.

2. The method of claim 1, wherein the composition comprises a mixture of about 79% to about 81% by weight of monomeric 2-octyl cyanoacrylate, about 21% to about 19% by weight of monomeric n-butyl cyanoacrylate, about 2000 ppm to about 14,000 ppm of butylated hydroxyl anisole, and about 10 ppm to about 200 ppm of sulfur dioxide.

3. The method of claim 1, wherein the composition comprises a mixture of about 79% to about 81% by weight of monomeric 2-octyl cyanoacrylate, about 21% to about 19% by weight of monomeric n-butyl cyanoacrylate, about 2000 ppm to about 8000 ppm of butylated hydroxyl anisole, and about 10 ppm to about 200 ppm of sulfur dioxide.

4. The method of claim 1, wherein the composition comprises a mixture of about 80% by weight of monomeric 2-octyl cyanoacrylate, about 20% by weight of monomeric n-butyl cyanoacrylate, about 2000 ppm to about 14,000 ppm of butylated hydroxyl anisole, and about 10 ppm to about 200 ppm of sulfur dioxide.

5. The method of claim 1, further comprising re-applying the cyanoacrylate adhesive composition to the skin after a period of time, and allowing the re-applied composition to cure on the skin.

6. The method of claim 1, wherein the composition further comprises about 10 ppm to about 150 ppm of a polymerization accelerator.

7. The method of claim 6, wherein the polymerization accelerator is a crown ether.

8. The method of claim 1, wherein viscosity of the composition increases no more than about 200% after sterilization.

9. The method of claim 1, wherein the viscosity of the sterilized composition increases no more than about 300% after about two years of shelf storage.

10. The method of claim 1, wherein the viscosity of the sterilized composition increases no more than about 250% after about two years of shelf storage.

11. The method of claim 1, wherein the viscosity of the sterilized composition increases no more than about 200% after about two years of shelf storage.

12. A method for inhibiting bacterial infection of the skin, comprising applying a cyanoacrylate adhesive composition to the skin and allowing the composition to cure on the skin, thereby reducing bacteria colonization on the skin, wherein the composition comprises a mixture of about 78% to about 82% by weight of monomeric 2-octyl cyanoacrylate, about 22% to about 18% by weight of monomeric n-butyl cyanoacrylate, about 2000 ppm to about 14,000 ppm of butylated hydroxyl anisole, and about 10 ppm to about 200 ppm of sulfur dioxide or about 5 ppm to about 50 ppm of an acid stabilizer selected from the group consisting of sulfuric acid, phosphoric acid, and perchloric acid, wherein the composition is sterilized by gamma irradiation, wherein the viscosity of the sterilized composition increases by no more than about 600% over a period of at least two years of shelf storage, and wherein the composition does not contain any plasticizer.

13. The method of claim 12, wherein the composition comprises a mixture of about 79% to about 81% by weight of monomeric 2-octyl cyanoacrylate, about 21% to about 19% by weight of monomeric n-butyl cyanoacrylate, about 2000 ppm to about 14,000 ppm of butylated hydroxyl anisole, and about 10 ppm to about 200 ppm of sulfur dioxide.

14. The method of claim 12, wherein the composition comprises a mixture of about 79% to about 81% by weight of monomeric 2-octyl cyanoacrylate, about 21% to about 19% by weight of monomeric n-butyl cyanoacrylate, about 2000 ppm to about 8000 ppm of butylated hydroxyl anisole, and about 10 ppm to about 200 ppm of sulfur dioxide.

15. The method of claim 12, wherein the composition comprises a mixture of about 80% by weight of monomeric 2-octyl cyanoacrylate, about 20% by weight of monomeric n-butyl cyanoacrylate, about 2000 ppm to about 14,000 ppm of butylated hydroxyl anisole, and about 10 ppm to about 200 ppm of sulfur dioxide.

16. The method of claim 12, wherein the composition further comprises about 10 ppm to about 150 ppm of a polymerization accelerator.

17. The method of claim 12, further comprising re-applying the cyanoacrylate adhesive composition to the skin after a period of time, and allowing the re-applied composition to cure on the skin.

18. A method for inhibiting bacterial infection of the skin, comprising applying a cyanoacrylate adhesive composition to the skin and allowing the composition to cure on the skin, thereby reducing bacteria colonization on the skin, wherein the composition comprises a mixture of about 80% by weight of monomeric 2-octyl cyanoacrylate, about 20% by weight of monomeric n-butyl cyanoacrylate, about 2000 ppm to about 8000 ppm of butylated hydroxyl anisole, and about 10 ppm to about 200 ppm of sulfur dioxide or about 5 ppm to about 50 ppm of an acid stabilizer selected from the group consisting of sulfuric acid, phosphoric acid, and perchloric acid, wherein the composition is sterilized by ethylene oxide exposure or irradiation, the viscosity of the composition increases no more than 200% after sterilization, and wherein the sterilized composition has at least two years of shelf stability as measured by an American Society for Testing and Materials (ASTM) accelerated aging standard, and wherein the composition does not contain any plasticizer or antimicrobial agent.

* * * * *